United States Patent
Austin et al.

(10) Patent No.: US 6,790,671 B1
(45) Date of Patent: Sep. 14, 2004

(54) OPTICALLY CHARACTERIZING POLYMERS

(75) Inventors: Robert H. Austin, Princeton, NJ (US); Jonas O. Tegenfeldt, Princeton, NJ (US); Eugene Y. Chan, Boston, MA (US)

(73) Assignee: Princeton University, Princeton, NJ (US)

(*) Notice: Subject to any disclaimer, the term of this patent is extended or adjusted under 35 U.S.C. 154(b) by 0 days.

(21) Appl. No.: 09/373,822

(22) Filed: Aug. 13, 1999

Related U.S. Application Data

(60) Provisional application No. 60/120,414, filed on Feb. 14, 1999, and provisional application No. 60/096,544, filed on Aug. 13, 1998.

(51) Int. Cl.[7] ................................................ C12Q 1/68

(52) U.S. Cl. ..................... 436/172; 436/94; 436/164; 436/177; 422/82.01; 422/82.05; 422/82.08; 422/82.12; 204/155; 204/603; 250/458.1; 250/461.1; 250/461.2; 356/344; 435/6; 435/808

(58) Field of Search ........................... 436/94, 164, 177, 436/172; 422/82.01, 82.05, 82.08, 82.12; 204/299, 182 B, 155, 603; 250/458.1, 461.1, 461.2; 356/344; 435/808, 6

(56) References Cited

U.S. PATENT DOCUMENTS

| | | | |
|---|---|---|---|
| 5,062,942 A | * 11/1991 | Kambara et al. | ........... 204/299 |
| 5,427,663 A | 6/1995 | Austin et al. | |
| 5,837,115 A | 11/1998 | Austin et al. | |
| 6,210,973 B1 | * 4/2001 | Pettit | .......................... 436/172 |
| 6,214,246 B1 | * 4/2001 | Craighead | .................... 216/56 |
| 6,263,286 B1 | * 7/2001 | Gilmanshin et al. | .......... 702/19 |
| 6,355,420 B1 | 3/2002 | Chan | |

* cited by examiner

*Primary Examiner*—Jill Warden
*Assistant Examiner*—Monique T. Cole
(74) *Attorney, Agent, or Firm*—Nixon Peabody, LLP

(57) ABSTRACT

The invention relates to new systems, methods and products for analyzing polymers and in particular new systems, methods and products useful for obtaining sequence information from polymers. The invention has numerous advantages over prior art systems and methods used to obtain sequence-related information. Using the methods of the invention the entire human genome could be analyzed several orders of magnitude faster than could be accomplished using conventional technology. In addition to obtaining sequencing information for the entire genome, the systems, methods and products of the invention can be used to create comprehensive and multiple expression maps for developmental and disease processes. The ability to analyze an individual's genome and to generate multiple expression maps will greatly enhance the ability to determine the genetic basis of any phenotypic trait or disease process.

51 Claims, 20 Drawing Sheets

FIG.15A 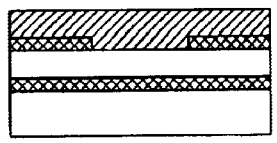 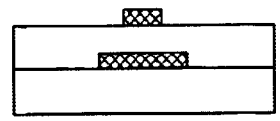 FIG.16A
FIG.15B 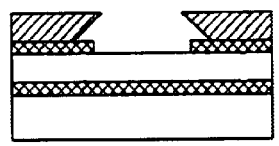 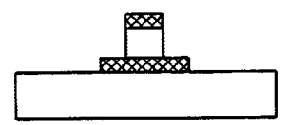 FIG.16B
FIG.15C 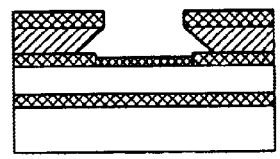 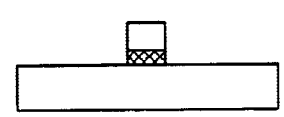 FIG.16C
FIG.15D 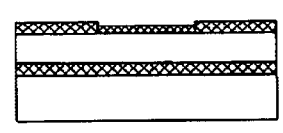 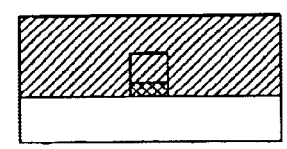 FIG.16D
FIG.15E 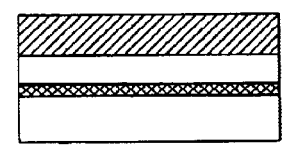 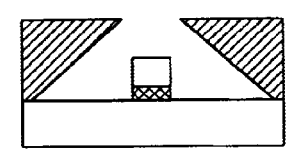 FIG.16E
FIG.15F 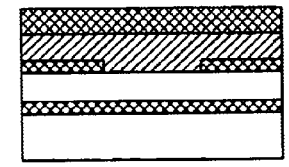 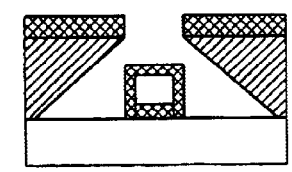 FIG.16F
FIG.15G 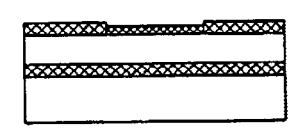 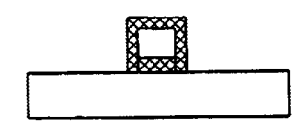 FIG.16G

OPTICALLY CHARACTERIZING POLYMERS

This patent application claims priority from U.S. Provisional Application No. 60/096,544 filed on Aug. 13, 1998, and U.S. Provisional Application No. 60/120,414 filed on Feb. 14, 1999, both of which are incorporated by reference.

FIELD OF THE INVENTION

The present invention is directed to optical systems, methods and products for analyzing polymers, and more particularly to optical systems, methods and products that utilize highly localized optical radiation for characterizing individual units of polymers.

BACKGROUND

Cells have a complex microstructure that determine the functionality of the cell. Much of the diversity associated with cellular structure and function is due to the ability of a cell to assemble various building blocks into diverse chemical compounds. The cell accomplishes this task by assembling polymers from a limited set of building blocks referred to as monomers or units. The key to the diverse functionality of polymers is based in the primary sequence of the monomers within the polymer and is integral to understanding the basis for cellular function, such as why a cell differentiates in a particular manner or how a cell will respond to treatment with a particular drug.

The ability to identify the structure of polymers identifying their sequence of monomers is integral to the understanding of each active component and the role that component plays within a cell. By determining the sequences of polymers it is possible to generate expression maps, to determine what proteins are expressed, to understand where mutations occur in a disease state, and to determine whether a polysaccharide has better function or loses function when a particular monomer is absent or mutated.

Expression maps relate to determining mRNA expression patterns. The need to identify differentially expressed mRNAs is critical in the understanding of genetic programming, both temporally and spatially. Different genes are turned on and off during the temporal course of an organisms' life development, comprising embryonic, growth, and aging stages. In addition to developmental changes, there are also temporal changes in response to varying stimuli such as injury, drugs, foreign bodies, and stress. The ability to chart expression changes for specific sets of cells in time either in response to stimuli or in growth allows the generation of what are called temporal expression maps. On the other hand, there are also body expression maps, which include knowledge of differentially expressed genes for different tissues and cell types. Since generation of expression maps involve the sequencing and identification of CDNA or mRNA, more rapid sequencing necessarily means more rapid generation of multiple expression maps.

Currently, only 1% of the human genome and an even smaller amount of other genomes have been sequenced. In addition, only one very incomplete human body expression map using expressed sequence tags has been achieved (Adams et al., 1995). Current protocols for genomic sequencing are slow and involve laborious steps such as cloning, generation of genomic libraries, colony picking, and sequencing. The time to create even one partial genomic library is on the order of several months. Even after the establishment of libraries, there are time lags in the preparation of DNA for sequencing and the running of actual sequencing steps. Given the multiplicative effect of these unfavorable facts, it is evident that the sequencing of even one genome requires an enormous investment of money, time, and effort.

In general, DNA sequencing is performed using one of two methods. The first and more popular method is the dideoxy chain termination method described by Sanger et al. ("DNA sequencing with chain-terminating inhibitors," *Proc. Natl. Acad. Sci. USA.* 74:5463–7, 1977). This method involves the enzymatic synthesis of DNA molecules terminating in dideoxynucleotides. By using the four ddNTPs, a population of molecules terminating at each position of the target DNA can be synthesized. Subsequent analysis yields information on the length of the DNA molecules and the base at which each molecule terminates (either A, C, G, or T). With this information, the DNA sequence can be determined. The second method is Maxam and Gilbert sequencing (Maxam and Gilbert, "A new method for sequencing DNA," *Proc. Natl. Acad. Sci. USA.* 74:560–4, 1977), which uses chemical degradation to generate a population of molecules degraded at certain positions of the target DNA. With knowledge of the cleavage specificities of the chemical reactions and the lengths of the fragments, the DNA sequence is generated. Both methods rely on polyacrylamide gel electrophoresis and photographic visualization of the radioactive DNA fragments. Each process takes about 1–3 days. The Sanger sequencing reactions can only generate 300–800 bases in one run.

Sanger-based methods have been proposed to improve the output of sequence information. The Sanger-based methods include multiplex sequencing, capillary gel electrophoresis, and automated gel electrophoresis. Recently, there has also been increasing interest in developing Sanger independent methods as well. Sanger independent methods use a completely different methodology to realize the base information. This category contains the most novel techniques, which include scanning electron microscopy (STM), mass spectrometry, enzymatic luminometric inorganic pyrophosphate detection assay (ELIDA) sequencing, exonuclease sequencing, and sequencing by hybridization.

Currently, automated gel electrophoresis is the most widely used method of large-scale sequencing. Automation requires reading of fluorescently labeled Sanger fragments in real time with a charge coupled device (CCD) detector. The four different dideoxy chain termination reactions are run with different labeled primers. The reaction mixtures are combined and co-electrophoresed down a slab of polyacrylamide. Using laser excitation at the end of the gel, the separated DNA fragments are resolved and the sequence determined by computer. Many automated machines are available commercially, each employing different detection methods and labeling schemes. The most efficient of these is the Applied Biosystems Model 377XL, which generates a maximum actual rate of 115,200 bases per day.

In the method of capillary gel-electrophoresis, reaction samples are analyzed by small diameter, gel-filled capillaries. The small diameter of the capillaries (50 $\mu$m) allows for efficient dissipation of heat generated during electrophoresis. Thus, high field strengths can be used without excessive Joule heating (400 V/m), lowering the separation time to about 20 minutes per reaction run. Not only are the bases separated more rapidly, there is also increased resolution over conventional gel electrophoresis. Furthermore, many capillaries are analyzed in parallel (Wooley and Mathies, "Ultra-high-speed DNA sequencing using capillary electrophoresis chips," *Anal. Chem.* 67:3676–3680, 1995), allowing amplification of base information generated (actual rate is equal to 200,000 bases/day). The main drawback is that there is not continuous loading of the capillaries since a new gel-filled capillary tube must be prepared for each reaction. Capillary gel electrophoresis machines have recently been commercialized.

Multiplex sequencing is a method which more efficiently uses electrophoretic gels (Church and Kieffer-Higgins, "Multiplex DNA sequencing," *Science*. 240:185–88, 1988). Sanger reaction samples are first tagged with unique oligomers and then up to 20 different samples are run on one lane of the electrophoretic gel. The samples are then blotted onto a membrane. The membrane is then sequentially probed with oligomers that correspond to the tags on the Sanger reaction samples. The membrane is washed and reprobed successively until the sequences of all 20 samples are determined. Even though there is a substantial reduction in the number of gels run, the washing and hybridizing steps are as equally laborious as running electrophoretic gels. The actual sequencing rate is comparable to that of automated gel electrophoresis.

Sequencing by mass spectrometry was first introduced in the late 80's. Recent developments in the field have allowed for better sequence determination (Crain, *MassSpectrom. Rev.* 9:505–54, 1990; Little et al., *J. Am. Chem. Soc.* 116:4893–4897, 1994; Keough et al., *Rapid Commun. Mass Spectrom.* 7:195–200,1993; Smirnov et al., 1996). Mass spectrometry sequencing first entails creating a population of nested DNA molecules that differ in length by one base. Subsequent analysis of the fragments is performed by mass spectrometry. In one example, an exonuclease is used to partially digest a 33-mer (Smirnov, "Sequencing oligonucleotides by exonuclease digestion and delayed extraction matrix-assisted laser desorption ionization time-of-flight mass spectrometry," *Anal. Biochem.* 238:19–25, 1996). A population of molecules with similar 5' ends and varying points of 3' termination is generated. The reaction mixture is then analyzed. The mass spectrometer is sensitive enough to distinguish mass differences between successive fragments, allowing sequence information to be generated.

Mass spectrometry sequencing is highly accurate, inexpensive, and rapid compared to conventional methods. The major limitation, however, is that the read length is on the order of tens of bases. Even the best method, matrix-assisted laser desorption ionization time-of-flight (MALDI-TOF) mass spectroscopy (Smirnov et al., "Sequencing oligonucleotides by exonuclease digestion and delayed extraction matrix-assisted laser desorption ionization time-of-flight mass spectrometry," *Anal. Biochem.* 238:19–25, 1996), can only achieve maximum read lengths of 80–90 base pairs. Much longer read lengths are physically impossible due to fragmentation of longer DNA at guanidines during the analysis step. Mass spectrometry sequencing is thus limited to verifying short primer sequences and has no practical application in large-scale sequencing.

The Scanning tunneling microscope (STM) sequencing (Ferrell, "Scanning tunneling microscopy in sequencing of DNA." In *Molecular Biology and Biotechnology*, R. A. Meyers, Ed. VCH Publishers, New York, 1997) method was conceived at the time the STM was commercially available. The initial promise of being able to read base-pair information directly from the electron micrographs no longer holds true. DNA molecules must be placed on conducting surfaces, which are usually highly ordered pyrolytic graphite (HOPG) or gold. These lack the binding sites to hold DNA strongly enough to resist removal by the physical and electronic forces exerted by the tunneling tip. With difficulty, DNA molecules can be electrostatically adhered to the surfaces. Even with successful immobilization of the DNA, it is difficult to distinguish base information because of the extremely high resolutions needed. With current technology, purines can be distinguished from pyrimidines, but the individual purines and pyrimidines cannot be identified. The ability to achieve this feat requires electron microscopy to be able to distinguish between aldehyde and amine groups on the purines and the presence or absence of methyl groups on the pyrimidines.

Enzymatic luminometric inorganic pyrophosphate detection assay (ELIDA) sequencing uses the detection of pyrophosphate release from DNA polymerization to determine the addition of successive bases. The pyrophosphate released by the DNA polymerization reaction is converted to ATP by ATP sulfurylase and the ATP production is monitored continuously by firefly luciferase. To determine base specificity, the method uses successive washes of ATP, CTP, GTP, and TTP. If a wash for ATP generates pyrophosphate, one or more adenines are incorporated. The number of incorporated bases is directly proportional to the amount of pyrophosphate generated. Enhancement of generated sequence information can be accomplished with parallel analysis of many ELIDA reactions simultaneously.

Exonuclease sequencing involves a fluorescently labeled, single-stranded DNA molecule which is suspended in a flowing stream and sequentially cleaved by an exonuclease. Individual fluorescent bases are then released and passed through a single molecule detection system. The temporal sequence of labeled nucleotide detection corresponds to the sequence of the DNA (Ambrose et al., "Application of single molecule detection to DNA sequencing and sizing," *Ber. Bunsenges. Phys. Chem.* 97:1535–1542, 1993; Davis et al., "Rapid DNA sequencing based on single-molecule detection," *Los Alamos Science.* 20:280–6, 1992; Jett et al., "High-speed DNA sequencing: an approach based upon fluorescence detection of single molecules," *J. Of Bio. Structure & Dynamics.* 7:301–9, 1989). Using a processive exonuclease, it theoretically is possible to sequence 10,000 bp or larger fragments at a rate of 10 bases per second.

In the sequencing by hybridization method, a target DNA is sequentially probed with a set of oligomers consisting of all the possible oligomer sequences. The sequence of the target DNA is generated with knowledge of the hybridization patterns between the oligomers and the target (Bains, "Hybridization methods for DNA sequencing," *Genomics.* 11:294–301, 1991; Cantor et al., "Reporting on the sequencing by hybridization workshop," *Genomics.* 13:1378–1383, 1992; Drmanac et al., "Sequencing by hybridization." In *Automated DNA Sequencing and Analysis Techniques*, J. Craig Ventor, Ed. Academic Press, London, 1994). There are two possible methods of probing target DNA. The "Probe Up" method includes immobilizing the target DNA on a substrate and probing successively with a set of oligomers. "Probe Down" on the other hand requires that a set of oligomers be immobilized on a substrate and hybridized with the target DNA. With the advent of the "DNA chip," which applies microchip synthesis techniques to DNA probes, arrays of thousands of different DNA, probes can be generated on a 1 $cm^2$ area, making Probe Down methods more practical. Probe Up methods would require, for an 8-mer, 65,536 successive probes and washings, which would take an enormous amount of time. On the other hand, Probe Down hybridizations generates data in a few seconds. With perfect hybridization, 65,536 October probes would determine a maximum of 170 bases. With 65,536 "mixed" 11-mers, 700 bases can be generated.

The most common limitation of most of these techniques is a short read length. In practice a short read length means that additional genetic sequence information needs to be sequenced before the linear order of a target DNA can be deciphered. The short fragments have to be bridged together with additional overlapping fragments. Theoretically, with a 500 base read length, a minimum of $9 \times 10^9$ bases need to be sequenced before the linear sequence of all $3 \times 10^9$ bases of the human genome are properly ordered. In reality, the number of bases needed to generate a believable genome is approximately $2 \times 10^{10}$ bases. Comparisons of the different techniques show that only the impractical exonuclease sequencing has the theoretical capability of long read lengths. The other methods have short theoretical read lengths and even shorter realistic read lengths. To reduce the number of bases that need to be sequenced, it is clear that the read length must be improved.

Protein sequencing generally involves chemically induced sequential removal and identification of the terminal amino acid residue, e.g., by Edman degradation. See Stryer, L., *Biochemistry*, W. H. Freeman and Co., San Francisco (1981) pp. 24–27. Edman degradation requires that the polypeptide have a flee amino group which is reacted with an isothiocyanate. The isothiocyanate is typically phenyl isothiocyanate. The adduct intramolecularly reacts with the nearest backbone amide group of the polymer thereby forming a five membered ring. This adduct rearranges and the terminal amino acid residue is then cleaved using strong acid. The released phenylthiohydantoin (PTH) of the amino acid is identified and the shortened polymer can undergo repeated cycles of degradation and analysis.

Further, several new methods have been described for carboxy terminal sequencing of polypeptides. See Inglis, A. S., Anal. Biochem. 195:183–96 (1991). Carboxy terminal sequencing methods mimic Edman degradation but involve sequential degradation from the opposite end of the polymer. See Inglis, A. S., Anal. Biochem. 195:183–96 (1991). Like Edman degradation, the carboxy-terminal sequencing methods involve chemically induced sequential removal and identification of the terminal amino acid residue.

More recently, polypeptide sequencing has been described by preparing a nested set (sequence defining set) of polymer fragments followed by mass analysis. See Chait, B. T. et al., Science 257:1885–94 (1992). Sequence is determined by comparing the relative mass difference between fragments with the known masses of the amino acid residues. Though formation of a nested (sequence defining) set of polymer fragments is a requirement of DNA sequencing, this method differs substantially from the conventional protein sequencing method consisting of sequential removal and identification of each residue. Although this method has potential in practice it has encountered several problems and has not been demonstrated to be an effective method.

Each of the known methods for sequencing polymers has drawbacks. For instance most of the methods are slow and labor intensive. The gel based DNA sequencing methods require approximately 1 to 3 days to identify the sequence of 300–800 units of a polymer. Methods such as mass spectroscopy and ELIDA sequencing can only be performed on very short polymers.

A need exists for de noveau polymer sequence determination. The rate of sequencing has limited the capability to generate multiple body and temporal expression maps which would undoubtedly aid the rapid determination of complex genetic function. A need also exists for improved systems and methods for analyzing polymers in order to speed up the rate at which diagnosis of diseases and preparation of new medicines is carried out.

SUMMARY OF THE INVENTION

The invention relates to new systems, methods and products for analyzing polymers and in particular new systems, methods and products useful for determining the sequence of polymers. The invention has numerous advantages over prior art systems and methods used to sequence polymers. Using the methods of the invention the entire human genome could be sequenced several orders of magnitude faster than could be accomplished using conventional technology. In addition to sequencing the entire genome, the systems, methods and products of the invention can be used to create comprehensive and multiple expression maps for developmental and disease processes. The ability to sequence an individual's genome and to generate multiple expression maps will greatly enhance the ability to determine the genetic basis of any phenotypic trait or disease process.

According to one aspect, a system for optically analyzing a polymer of linked units includes an optical source, an interaction station, an optical detector, and a processor. The optical source is constructed to emit radiation of a selected wavelength. The interaction station is constructed to receive the emitted radiation and produce a localized radiation spot from the radiation emitted from the optical source. The interaction station is also constructed to sequentially receive units of the polymer and arranged to irradiate sequentially the units at the localized radiation spot. The optical detector is constructed to detect radiation including characteristic signals resulting from interaction of the localized radiation spot with the units. The processor is constructed andy arranged to analyze the polymer based on the detected radiation.

Preferred embodiments of this aspect include one or more of the following features:

The interaction station is constructed to sequentially receive the units being selectively labeled with a radiation sensitive label and the interaction includes interaction of the localized radiation with the radiation sensitive label.

The radiation sensitive label includes a fluorophore.

The interaction station includes a constructed to receive the emitted radiation and provide the evanescent radiation in response thereto.

The interaction station includes a slit having a width in the range of 1 nm to 500 nm, wherein the slit produces the localized radiation spot.

The interaction station includes a microchannel and a slit having a submicron width arranged to produce the localized radiation spot. The microchannel is constructed to receive and advance the polymer units through the localized radiation spot.

The width of the slit is in the range of 10 nm to 100 nm.

The system may include a polarizer and the optical source is a laser constructed to emit a beam of radiation and the polarizer is arranged to polarize the laser beam prior to reaching the slit.

The polarizer may be arranged to polarize the laser beam in parallel to the width of the slit, or perpendicular to the width of the slit.

The interaction station may include several slits located perpendicular to the microchannel that is arranged to receive the polymer in a straightened form.

The interaction station may include a set of electrodes constructed and arranged to provide electric field for advancing the units of the polymer through the microchannel.

The system may further include an alignment station constructed and arranged to straighten the polymer and provide the straightened polymer to the interaction station.

In another embodiment a method for optically analyzing a polymer of linked units comprising:

labeling selected units of the polymer with radiation sensitive labels;

sequentially passing the units of the polymer through a microchannel;

generating radiation of a selected wavelength to produce therefrom a localized radiation spot;

irradiating sequentially the labeled units of the polymer at the localized radiation spot;

detecting sequentially radiation providing characteristic signals resulting from interactions of the localized radiation spot with the labels or the units; and analyzing the polymer based on the detected radiation.

In another embodiment, an article of manufacture used for optically analyzing a polymer of linked units, comprising an interaction station fabricated on a substrate and constructed to receive radiation and produce therefrom a localized radiation spot. The interaction station is further constructed to sequentially receive units of the polymer and arranged to irradiate sequentially the units at the localized radiation spot to generate characteristic signals of radiation.

According to another aspect, a system for optically analyzing a polymer of linked units includes an optical source, an interaction station, an optical detector, and a processor. The optical source is constructed to emit radiation of a selected wavelength. The interaction station is constructed to receive the emitted radiation and constructed to sequentially receive units of the polymer and arranged to irradiate sequentially the units of the polymer with evanescent radiation excited by the radiation emitted from the source. The optical detector is constructed to detect radiation including characteristic signals resulting from interaction of the evanescent radiation with the units. The processor is constructed and arranged to analyze the polymer based on the detected radiation.

Preferred embodiments of this aspect include one or more of the following features:

The interaction station is constructed to sequentially receive the units being selectively labeled with a radiation sensitive label and the interaction includes interaction of the evanescent radiation with the radiation sensitive label.

The radiation sensitive label includes a fluorophore.

The interaction station includes a waveguide constructed to receive the emitted radiation and provide the evanescent radiation in response thereto.

The waveguide is a dielectric waveguide constructed to achieve total internal reflection of introduced light. The waveguide is a rectangular mirror waveguide with a dielectric surrounded by metallic mirror layers constructed to have a low loss of introduced light. The waveguide includes a tip including an aperture in the metallic mirror layers and arranged to emit the evanescent radiation. The waveguide includes a tip constructed to emit the evanescent radiation.

The interaction station includes a nanochannel located at the tip of the waveguide and arranged to receive the polymer in a straightened form.

The interaction station includes a set of electrodes constructed and arranged to provide electric field for advancing the units of the polymer through the nanochannel. The electrodes are internal electrodes.

The electrodes are external electrodes. The nanochannel is between 2 and 50 nanometers.

The waveguide is further constructed and arranged to receive the radiation including the characteristic signals and optically couple the received radiation to the optical detector.

The interaction station includes another waveguide constructed and arranged to receive the radiation including the characteristic signals and optically couple the received radiation to the optical detector.

The system further includes an alignment station constructed and arranged to straighten the polymer and provide the straightened polymer to the interaction station.

In yet another aspect the invention is a system for optically analyzing a polymer utilizing confocal fluorescence illumination of linked units. The system includes an optical source constructed to emit optical radiation; a filter constructed to receive and filter said optical radiation to a known wavelength; a dichroic mirror constructed to receive said filtered optical radiation; an interaction station constructed to receive said filtered optical radiation and produce a localized radiation spot from said filtered optical radiation, said interaction station being also constructed to sequentially receive units of said polymer and arranged to irradiate sequentially said units at said localized radiation spot; an optical detector constructed to detect radiation including characteristic signals resulting from interaction of said units at said localized radiation spot; and a processor constructed and arranged to analyze said polymer based on said detected radiation including said characteristic signals.

In one embodiment the interaction station is constructed to sequentially receive said units being selectively labeled with a radiation sensitive label producing said characteristic signals at said localized radiation spot. In another embodiment the radiation sensitive label includes a fluorophore. In some embodiments the filter is a laser line filter.

The system may also include an objective, wherein the objective focuses said filtered optical radiation.

The proposed system and method for analyzing polymers is particularly useful for determining the sequence of units within a DNA molecule and can eliminate the need for generating genomic libraries, cloning, and colony picking, all of which constitute lengthy pre-sequencing steps that are major limitations in current genomic-scale sequencing protocols. The methods disclosed herein provide much longer read lengths than achieved by the prior art and a million-fold faster sequence reading. The proposed read length is on the order of several hundred thousand nucleotides. This translates into significantly less need for overlapping and redundant sequences, lowering the real amount of DNA that needs to be sequenced before genome reconstruction is possible. The actual time taken to read a given number of units of a polymer is a million-fold more rapid than current methods because of the tremendous parallel amplification supplied by a novel apparatus also claimed herein, which is referred to as a nanochannel plate or a microchannel plate. The combination of all these factors translates into a method of polymer analysis including sequencing that will provide enormous advances in the field of molecular and cell biology.

BRIEF DESCRIPTION OF THE DRAWINGS

FIGS. 14A through 16G illustrate the fabrication of the optical waveguides shown in FIG. 11.

DETAILED DESCRIPTION OF THE PREFERRED EMBODIMENTS

Figure 1:
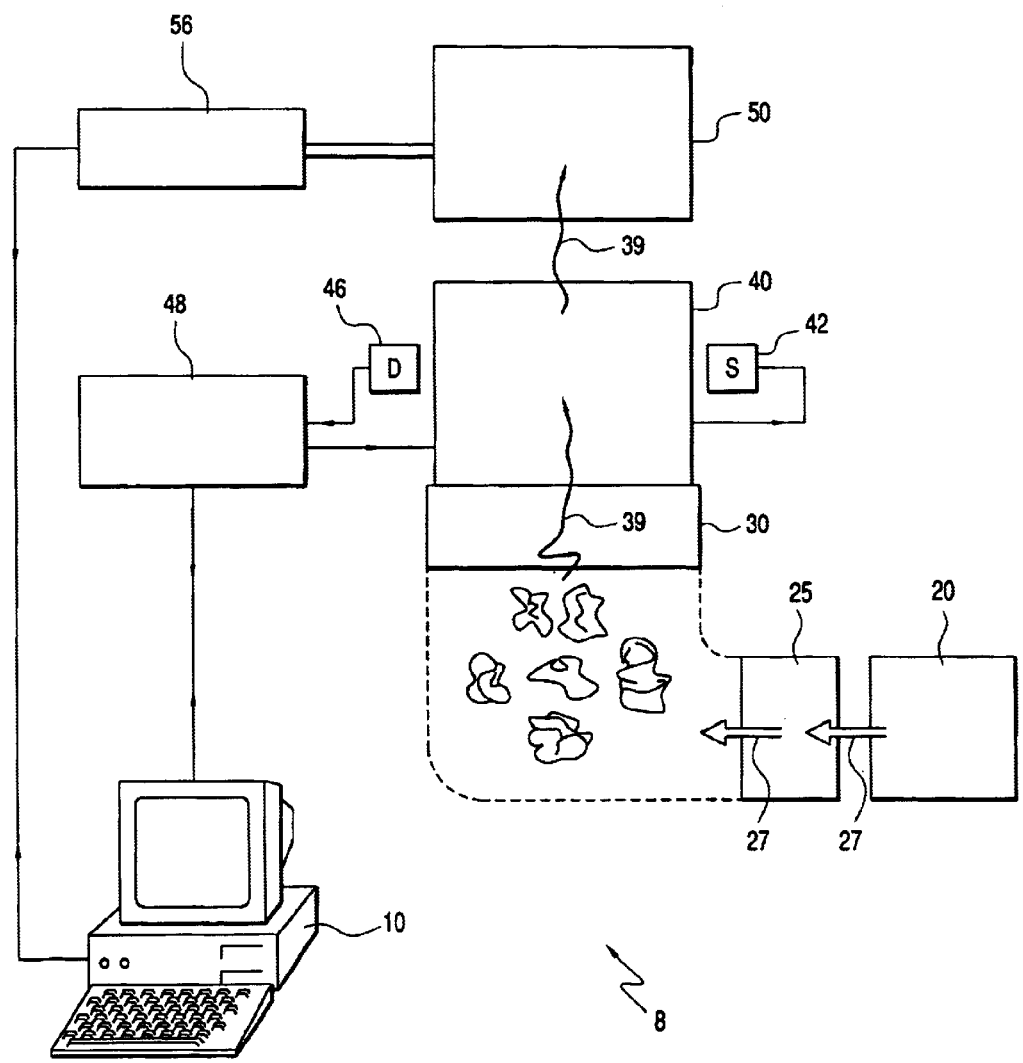
FIG. 1 illustrates diagrammatically a system for characterizing polymers.

Referring to FIG. 1, an interactive system for characterizing individual units of a polymer includes a system controller 10, a polymer supply 20, a microfluidic pump 25, a polymer alignment station 30, a first interaction station 40, and a second interaction station 50. System controller 10 may be a general purpose computer. Microfluidic pump 25 supplies selected amounts of polymer 27 from polymer supply 20 to polymer alignment station 30. Polymer alignment station 30, controlled by system controller 10, straightens and aligns individual polymers using force field and mechanical obstacles, and dispenses the polymers to first interaction station 40. The first interaction station 40 uses an optical system for characterizing individual units of the polymer passing through. The optical system includes an optical source 42, an optical filter 45, an optical detector 46 and other optical elements and electronic elements associated with the source and detector. The optical system is controlled by an optical controller 48.

As the individual units of in the polymer pass through interaction station 40, optical source 42 emits radiation directed to an optical component of interaction station 40. The optical component produces a localized radiation spot that interacts directly with polymer units, or interacts with labels selectively attached to the polymer units, or interact with both the polymer units and the labels. The localized radiation spot includes non-radiating near field or an evanescent wave, localized in at least one dimension. The localized radiation spot provides a much higher resolution than the diffraction-limited resolution used in conventional optics.

Furthermore, interaction station 40 uses unique arrangements and geometries that allow the localized radiation spot to interact with one or several polymer units or attached labels that are on the order of nanometers or smaller. Optical detector 46 detects light modified by the interaction and provides a detection signal to optical controller 48. Second interaction station 50 uses electric or electromagnetic field, X-ray radiation, or visible or infrared radiation for characterizing the polymer passing from first interaction station 40 through second interaction station 50. A controller 56 controls the operation of second interaction station 50. Both controllers 48 and 56 are connected to system controller 10.

Figure 2:
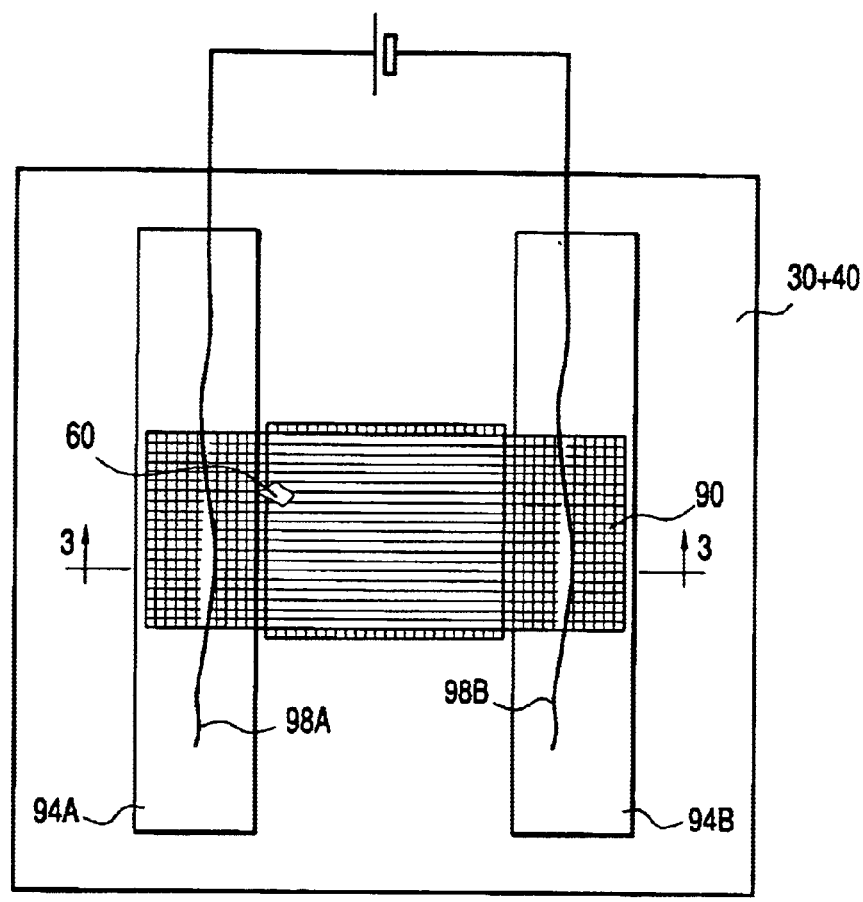
FIG. 2 illustrates an alignment and a first interaction station used in the system of FIG. 1.
Figure 3:
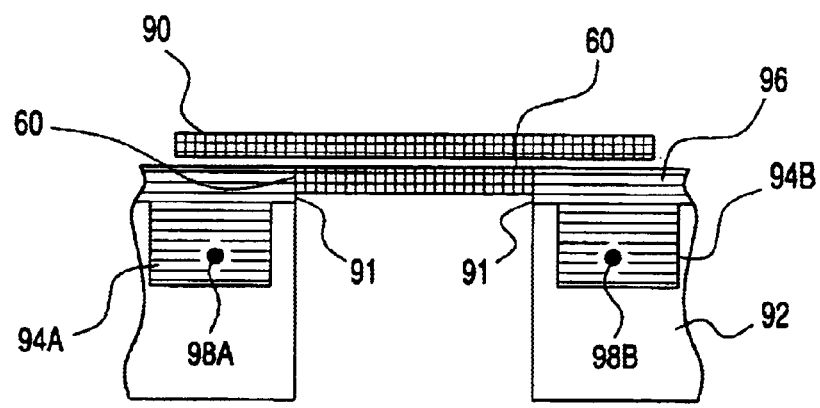
FIG. 3 is a cross-sectional view of the alignment and the first interaction station along lines 3—3 shown in FIG. 2.

Referring to FIGS. 2 and 3, polymer alignment station 30 and first interaction station 40 include a substrate 92, a quartz wafer 60, and a glass cover 90, which is optional. Substrate 92 is machined from a non-conducting, chemically inert material, such as Teflon® or Delrin®, to facilitate a flow of conducting fluid 96 (for example, agarose gel) and the examined polymer. Substrate 92 includes trenches 94A and 94B machined to receive gold wires 98A and 98B, respectively, which have a selected shape in accordance with the shape of the electric field used for advancing polymer molecules 39 across first interaction station 40. Quartz wafer 60 is sealed onto substrate 92 around regions 91.

Alternatively, trenches 94A and 94B and wires 98A and 98B may be replaced by metallic regions located directly on quartz wafer 60, or may be replaced by external electrodes for creating the electric field. In general, the electrodes are spaced apart over a distance in the range of about millimeter to 5 centimeters, and preferably 2 centimeters and provide typically field strengths of about 20 V/cm.

Figure 4:
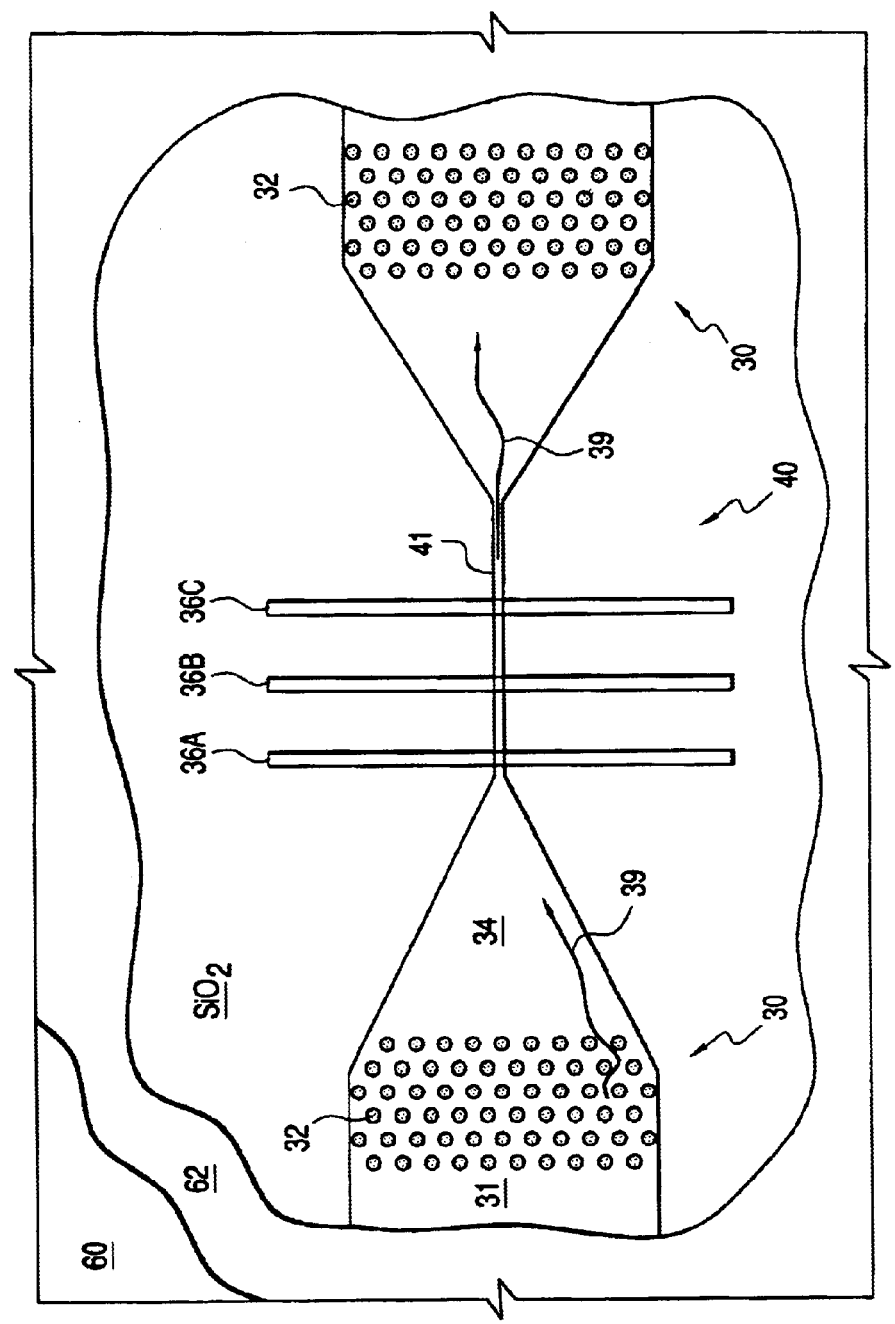
FIG. 4 is a top view of a portion of the alignment and the first interaction station shown in FIG. 2.
Figure 4A:
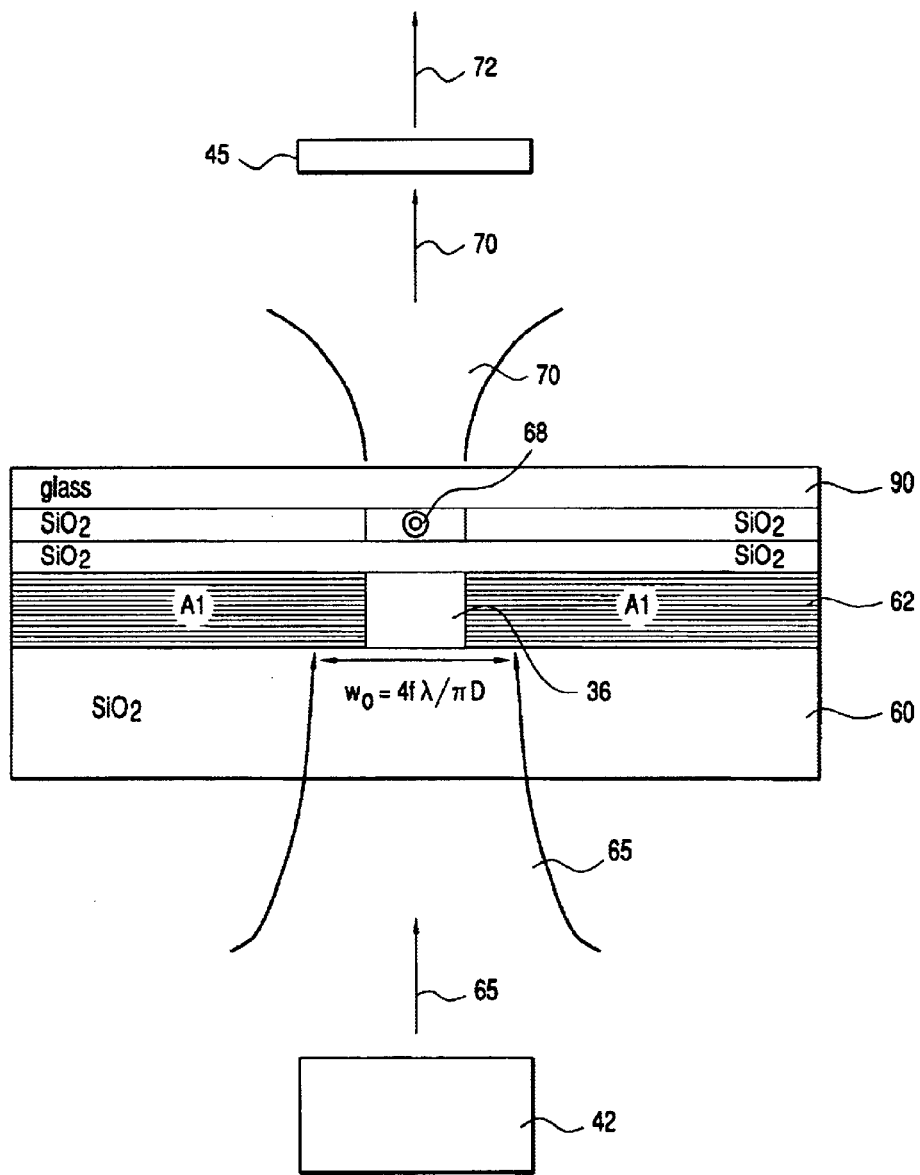
FIG. 4A illustrates the arrangement of a nanoslit located in the first interaction station shown in FIG. 4.

FIGS. 4 and 4A show a presently preferred embodiment of alignment station 30 and first interaction station 40. FIG. 4 is a top view of a portion of alignment station 30 and first interaction station 40 (also shown in FIG. 2), which are fabricated on quartz wafer 60. Of course, a single quartz wafer 60 may include hundreds or thousands of the alignment and first interaction stations. Quartz wafer 60 included a quartz substrate covered with a metal layer 62 (e.g., aluminum, gold, silver) and having a microchannel 41 fabricated on the surface. Fabricated through metal layer 62 are slits 36A, 36B and 36C, which form the optical elements that provide the localized radiation spot. Slits 36A, 36B and 36C have a selected width in the range between 1 nm and 5000 nm, and preferably in the range between 10 nm and 1000 nm, and more preferably in the range between 10 nm and 100 nm. Slits 36A, 36B and 36C are located across microchannel 41, which has a width in the range of 1 micrometer to 50 micrometers and a length of several hundred micrometers. The electric field, created by gold wires 98A and 98B, pulls a polymer chain 39 (such as a DNA molecule) through microchannel 41 past slits 36A, 36B and 36C.

As shown in FIG. 4, polymer alignment station 30 includes several alignment posts 32 located in regions 31. Regions 31 are connected via transition regions 34 to microchannel 41 Alignment posts 32 have a circular cross-section and are about 1 micron in diameter. Alignment posts 32 are spaced about 1.5 microns apart and located about 5 $\mu$m to 500 $\mu$m (and preferably about 10 $\mu$m to 200 $\mu$m) from microchannel 41 depending on the length of the examined polymer. For example, when the polymer is bacteriophage T4 DNA, which has about 167 000 base pairs, alignment posts 32 are located about 30 $\mu$m from nanoslit 36A. In general, the distance from nanoslit 36A is about one half of the expected length of polymer 39.

FIG. 4A illustrates interaction of a light beam 65, emitted from optical source 42, with a nanoslit 36, formed in metal layer 62, to produce a localized radiation spot 67. Laser beam 65, which has a size many times larger than the width of nanoslit 36, irradiates the back side of quartz wafer 60, propagates through quartz wafer 60 and interacts with nanoslit 36. Localized radiation spot 67, which is a non-radiating near field, irradiates sequentially the units of polymer chain 39 as polymer chain 39 is pulled through microchannel 41. Localized radiation spot 67 may be understood as an evanescent wave emitted from nanoslit 36. Because the width of nanoslit 36 is smaller than the wavelength of light beam 65 the radiation is in the Fresnel mode.

The optical system may also include a polarizer 43 placed between optical source 42 and quartz wafer 60, and a notch filter 45, placed between quartz wafer 60 and optical detector 46. When the polarizer orients light beam 65 with the E vector parallel to the length of nanoslit 36, there is near-field radiation emitted from nanoslit 36 and no far field radiation. When the polarizer orients light beam 65 with the E vector perpendicular to nanoslit 36 (which is many wavelengths long), there is far-field emission from nanoslit 36. By selectively polarizing the incident beam 65, the optical system can switch between the near-field and far-field emissions.

Figure 4B:
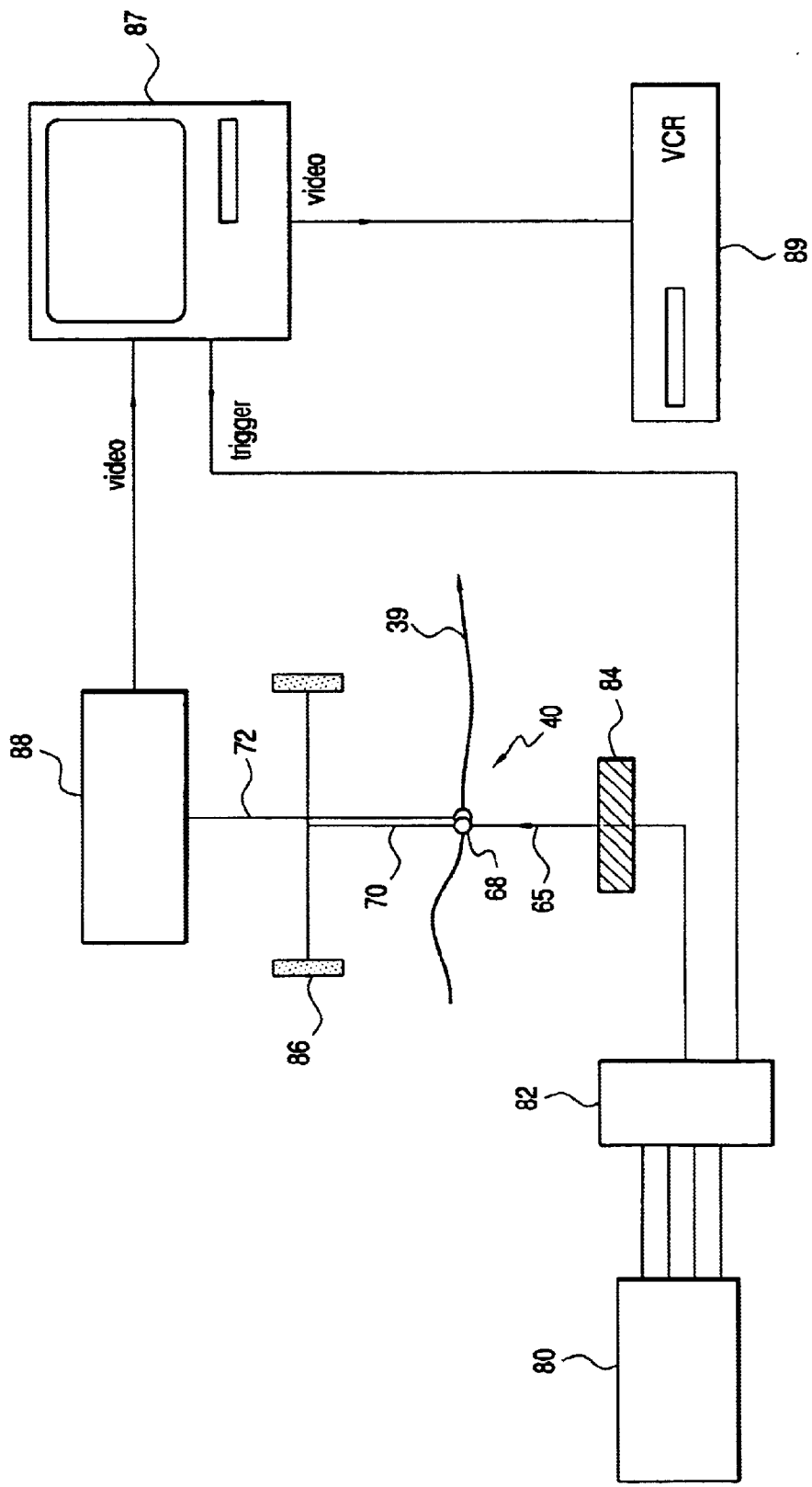
FIG. 4B illustrates an optical system for characterizing polymer units labeled by a fluorophore.

FIG. 4B illustrates an optical system for characterizing polymer units labeled by a fluorophore. The optical system includes a laser source 80, an acousto-optic tunable filter 82, a polarizer 84, a notch filter 86, an intensifier and a CCD detector 88, and a video monitor 87 connected to a video recorder VCR 89. The individual units of polymer chain 39 are selectively labeled by a fluorophore 68 sensitive to a selected excitation wavelength. Acousto-optic tunable filter 82 is used to select the excitation wavelength of the light emitted from laser source 80. The excitation beam 65 interacts with nanoslit 36 (shown in FIG. 4A and designated here as region 40) to create the non-radiating near-field 67. The electric field between gold wires 98A and 98B (FIGS. 2 and 3) pulls polymer chain 39 at a known rate causing interaction of each labeled unit with radiation 67. As fluorophore 68 moves pass slits 36A, 36B and 36C (shown FIG. 4), emitted radiation 67 excites fluorophore 68 that re-emits fluorescent radiation 72. Notch filter 86 passes the fluorescent wavelength 72 of radiation 70 and attenuates the excitation wavelength to increase the signal to noise resolution, as is known in the art. CCD detector 88 located few millimeters to few centimeters above quartz wafer 60 detects fluorescent radiation 72. CCD detector 88 can detect separately for each nanoslits 36A, 36B and 36C fluorescent radiation 72 as the fluorophore moves across. This process occurs at a large number of nanoslits located on quartz wafer 60.

Electric field may be used to position polymer 39 close to nanoslit 36. Nanoslit 36 "emits" the non-radiating field 67, which is attenuated over a distance of only one or two wavelengths. To position fluorophore 68 within the range of the non-radiating field 67, polymer 39 may need to be pulled closer to nanoslit 36 (and metal film 62) and thus closer to metal layer 62. Polymer 39 is pulled closer to nanoslit 36 using dielectric forces created by applying AC field to metal layer 62. See, e.g., "Trapping of DNA in Nonuniform Oscillating Electric Fields," by Charles L. Ashbury and Ger van den Engh, Biophysical Journal Vol 74, pp 1024–1030 (1998), "Molecular Dielectrophoresis of Biopolymers," by M. Washizu, S. Suzuki, O. Kurosawa, T. Nishizaka, and T. Shinohara, in IEEE Transactions on Industry Applications, Vol 30, No 4, pp. 835–843 (1994), and "Electrostatic Manipulation of DNA in Microfabricated Structures," by M. Washizu, and O. Kurosawa, in IEEE Transactions on Industry Applications, Vol 26, No 6, pp. 1165–1172 (1990). In general, see "Dielectrophoresis: The Behavior of Neutral Matter in Nonuniform Electric Fields," by Pohl, H. A., Cambridge University Press, Cambridge, UK, 1978. The inhomogeneous field will attract polarized units of polymer 39 (e.g., DNA molecule) to metal layer 62.

Figure 5:
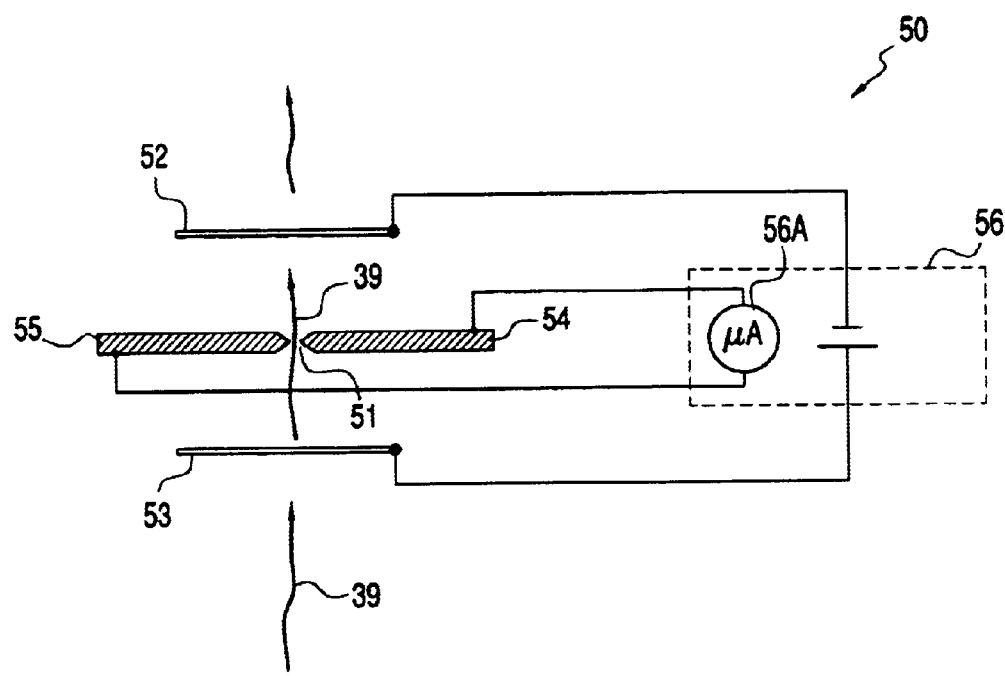
FIGS. 5 and 5A illustrate a second interaction station used in the system of FIG. 1.
Figure 5A:
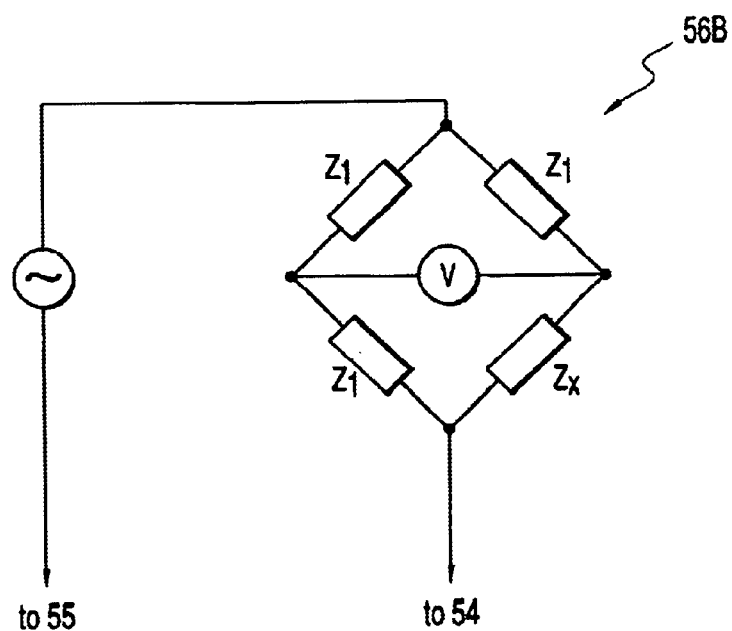

Referring to FIG. 5 second interaction station 50 measures ionic current across a nanochannel linearized polymer molecules approach the nanochannel and pass through. The detected blockages of the ionic current are used to characterize the length of the polymer molecules and characteristics of the polymer. Interaction station 50 receives linearized polymer 39 from first interaction region 40 and applies transchannel voltage using electrodes 52 and 53 in a direction perpendicular to electrodes 54 and 55 to draw the polymer molecules through a channel 51. Electrodes 54 and 55 are connected to a microampere meter 56A, located in controller 56, to measure the ionic current across nanochannel 51. Alternatively, referring to FIG. 5A, the microampere meter is replaced by a bridge 56B, which compares the impedance of channel 51 without polymer 39 ($Z_l$) with the instantaneous impedance of ($Z_x$). Without polymer 39 present in channel 51, the voltmeter measures 0 V. As the extended, nearly linear string 39 passes through channel 51, its presence detectably reduces, or completely blocks, the normal ionic flow from electrode 54 to electrode 55.

Electrodes 54 and 55 are fabricated using submicron lithography and are connected to the bridge to detect changes in the impedance or the microampere meter to measure the ionic current. The measured data across the channel are amplified, and the amplified signal is filtered (e.g., 64,000 samples per second) using a low pass filter, and the data is digitized at a selected sampling rate by an analog-to-digital converter. System controller 10 correlates the transient decrease in the ionic current with the speed of the polymer units and determines the length of the polymer, for example the length of a DNA or RNA molecule.

In another embodiment, the optical system includes an ultra fast, highly sensitive spectrophotometer capable of detecting fluorescence from a single fluorophore. Optical source 42 is a mode-locked Nd:YAG laser emitting radiation of an excitation wavelength. The system uses a splitter providing a reference beam to a photodiode and a discriminator (e.g., Tenneled TC454) that provides the start pulse to a time-to-amplitude converter (e.g., Tunnelec 863). The primary beam 65 is directed through a neutral density filter that adjusts the power level. As described above, fluorophore 68 interacting with non-radiation near-field 67 excites fluorescent light 72, which is collected by detector 46 after being spectrally filtered by an interference filter (e.g., made by Omega Optics) and detected by an avalanche photodiode or a photomultiplier (e.g., Hamamatsu R1562UMCP microchannel photomultiplier). The microchannel photomultiplier signal is amplified by an amplifier and shaped by a discriminator (for example, Tunnelec C4534 discriminator). The signal having appropriate time delays are provided to the time-to-amplitude converter (TAC). The time-gated TAC output is counted by a multiscaler and interfaced via a VME interface to system controller 10. System controller 10 provides, for the signal from each detector, a time-delay histogram that is characteristic for each type of the fluorescing fluorophore coupled to a unit of polymer 39.

Different fluorophores have different fluorescent lifetimes (i.e., the average amount of time that the molecule remains excited before returning to the ground electronic state through the emission of a fluorescent photon) that usually have an exponential probability distribution. Fluorescent lifetime is useful for identification of the fluorophore. In rapid sequencing, the system can use related dyes with similar spectra but different lifetimes thus employing only one laser source emitting the excitation wavelength and one detector detecting the fluorescent radiation.

In another embodiment, the optical system uses modulated radiation (e.g., single side band or double side band modulation) at frequencies in the range of 10 MHZ to 1 GHz using phase modulation techniques to characterize fluorescence of a single fluorophore located next to a polymer unit. For example, a laser source emits a light beam 65, which is intensity modulated using a sinusoidal signal at a frequency of 100 MHZ. The excited fluorescent radiation 72 is detected using a photomultiplier. The corresponding signal is homodyne or heterodyne detected to resolve the characteristic signal from the fluorophore, e.g., fluorescent lifetime. (See, for example, Lackowicz, J. R., "Gigahertz Frequency-Domain Fluorometry: Resolution of Complex Intensity Decays, Picosecond Processes and Future Developments," Photon Migration in Tissues, Academic Press, NY, pp.169–186, 1989; see also other references cited therein)

Figure 6:
FIGS. 6 through 7B illustrate the fabrication of the alignment and first interaction station shown in FIG. 4.
Figure 6A:
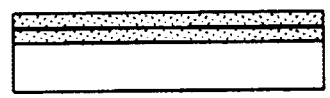
Figure 6B:
Figure 6C:
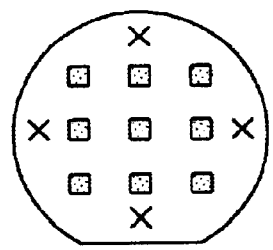
Figure 6D:
Figure 7:
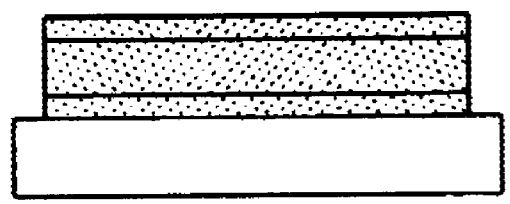
Figure 7A:
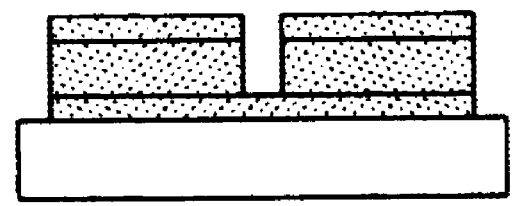
Figure 7B:
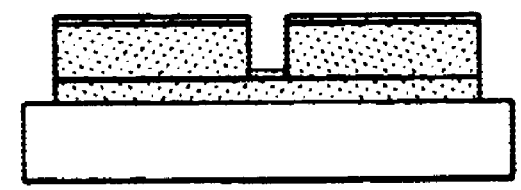

FIGS. 6 through 7B illustrate the fabrication of alignment region 30, microchannel 41 and slits 36A, 36B and 36C, shown in FIG. 4. FIG. 6 is a side view of quartz wafer 60, which is about 400 microns thick and polished on both sides. First a 300 nm thick aluminum film 62 is evaporated on the wafer and primed in hexamethyldisiloxane (HMDS) for 35 minutes (FIG. 6). Then, a photoresist Shipley 1813 was spun onto the wafers at 4000 rpm 60 sec., and the wafer was baked on a hotplate at 115° C. to harden the resist (FIG. 6A). The wafer was exposed, and the photoresist developed in 1:1 MF 312 developer and water for 60 seconds. The coarse aluminum pattern was etched using a Cl reactive ion etcher PK 1250 for 1.5 min. (FIG. 6B). FIG. 6C shows an overview of the wafer with the devices shown as squares and alignment marks as crosses. All resist residues were removed using the resist descum process in the Branson barrel etcher at 1000 W RF power for 10 minutes (FIG. 6D).

Figure 6E:
Figure 6F:
Figure 6G:
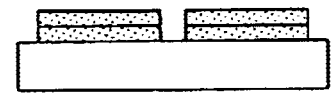
Figure 6H:
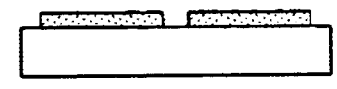
Figure 6I:
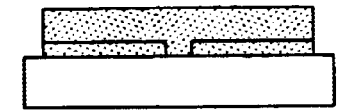

Referring to FIG. 6E, the PMMA resist (4% 950 K in MIBK) was spun onto the wafers at 3000 rpm for 60 seconds and the wafer was baked on a hotplate at 180° C. for 30 min. Then a 100 Å layer of gold was evaporated onto the PMMA photoresist to avoid a charge build-up. The PMMA photoresist was exposed in an e-beam system to define the nanoslits. The exposed PMMA resist was developed in IPA:MIBK 3:1 for 1 min, and the 100 Å layer of gold metal was etched (FIG. 6F). Next, the nanoslit patterns were defined by etching aluminum using the Cl reactive ion etch PK 1250 for 1.5 min (FIG. 6G). The photoresist was removed using the Branson barrel etcher at 1000 W RF power for 10 minutes (FIG. 6H). To create alignment region 30 and microchannel 41, a one micron layer of $SiO_2$ was deposited using plasmna enhanced chemical vapor deposition (PECVD) at T=240 C., 450 mTorr, 50 W RF power using 15 sccm silane, 50 sccm $N_2O$ (FIG. 6I). The $SiO_2$ layer was planarized by chemical mechanical polishing (CMP).

FIGS. 7 through 7B are side views of the wafer along one of the nanochanels. Referring to FIG. 7, alignment region 30 and microchannel 41 were defined by first spinning photoresist Shipley 1813 onto the wafers at 1800 rpm for 60 sec. and baking the resist on a hotplate at 115° C. for 60 sec. The resist was exposed in a high resolution mask aligner, such as a 5×g-line stepper, and developed in 1:1 MF 312 and water for 60 sec. The $SiO_2$ layer was etched (FIG. 7A) using reactive ion etching (RIE) in $CHF_3$ (50 sccm)+$O_2$ (2 sccm) to define the pattern in the $SiO_2$ layer as shown in FIG. 4. The photoresist was removed using the Branson barrel etcher at 1000 W RF power for 10 minutes. Next, a protective $SiO_2$ layer of 10 nm to 100 nm was deposited deposited PECVD (FIG. 7B). Glass cover 90 (shown in FIG. 2) may be anodically bonded to quartz wafer 60, or may be attached to chip 60 using a thin layer of RTV.

Figure 8:
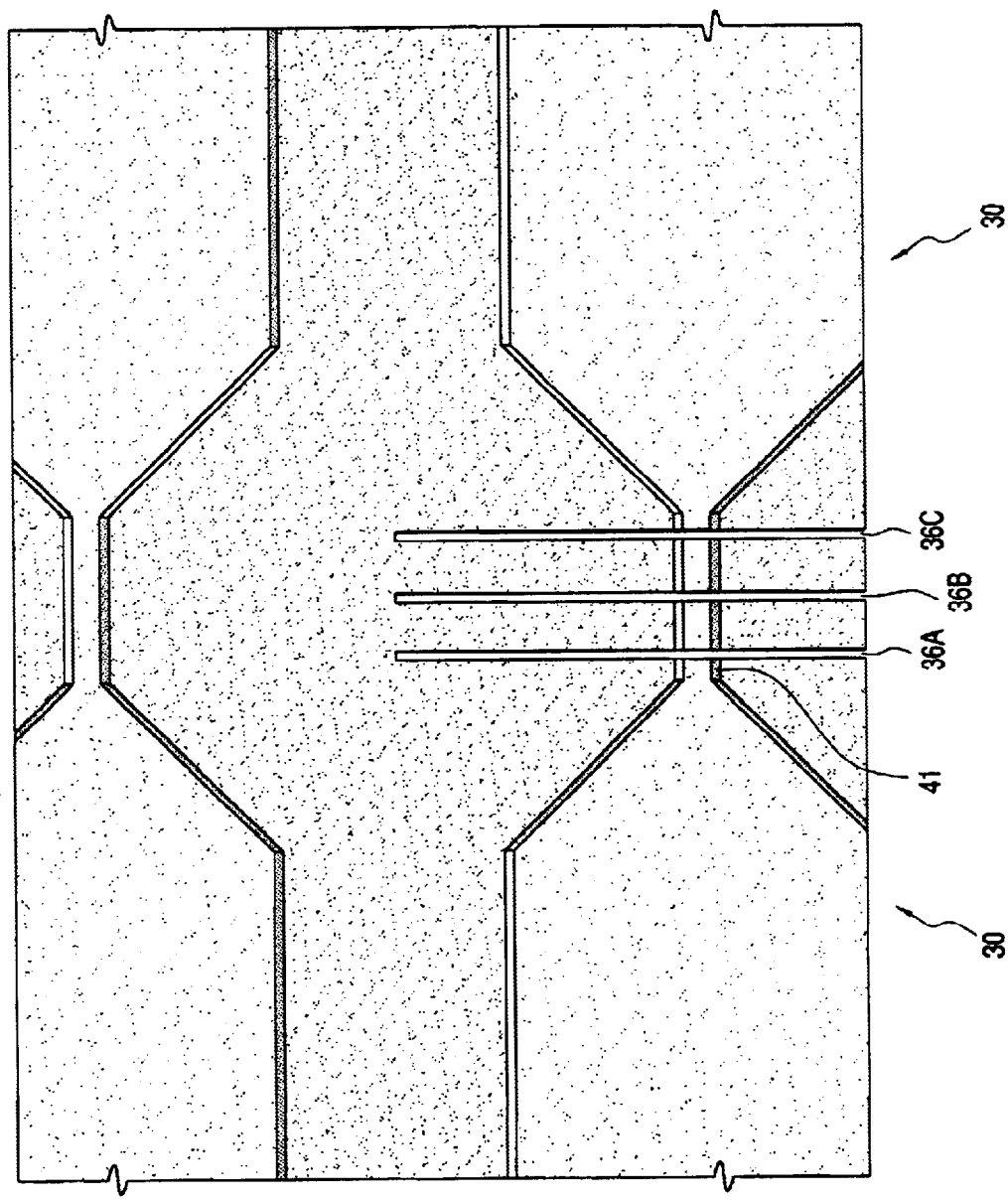
FIG. 8 is an SEM micrograph of the fabricated alignment and first interaction stations.

FIG. 8 shows an SEM micrograph with two fabricated alignment regions 30 and two interaction regions 40. Each alignment region 30 includes microposts 32, and each interaction region 40 includes microchannel 41 and nanoslits 36A, 36B, and 36C, as drawn in FIG. 4.

Figure 9:
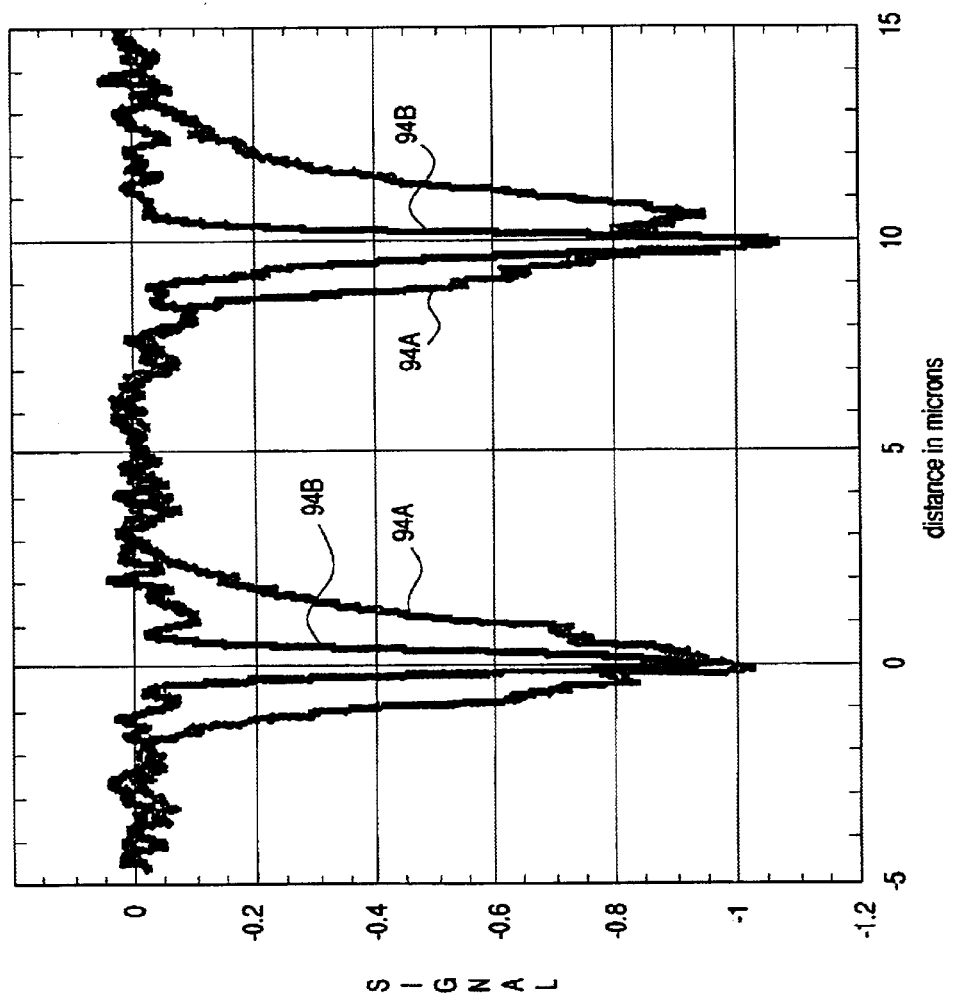
FIGS. 9, 10A, 10B, and 10C show results of a test measurement of the alignment and interaction station of FIG. 8.
Figure 10A:
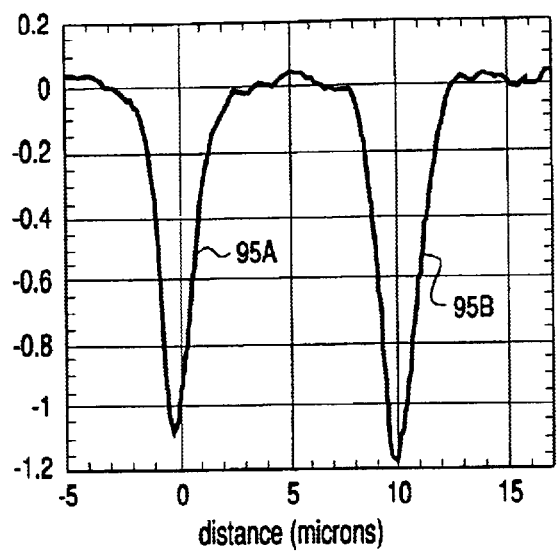
Figure 10B:
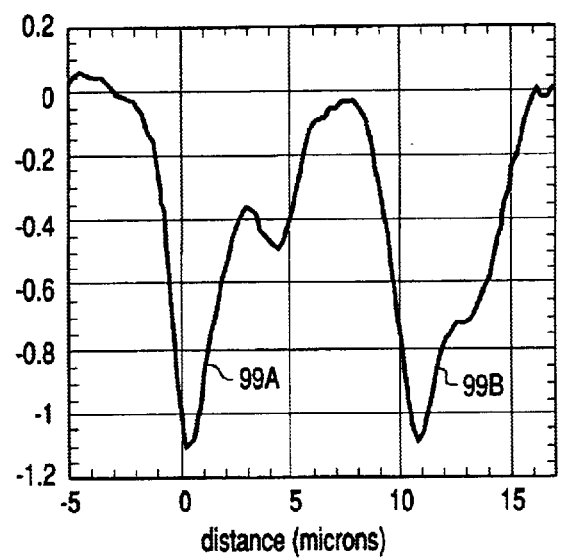
Figure 10C:
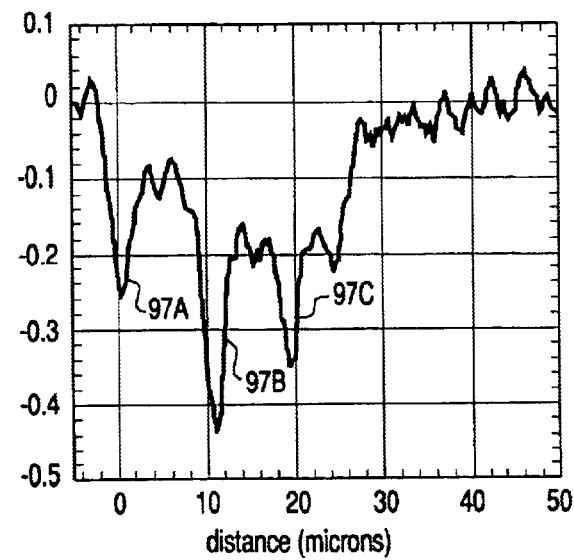

Referring to FIGS. 9 through 10C, the fabricated alignment regions 30 and interaction regions 40 (shown in FIG. 8) were tested in the following experiment. CW laser light from a collimated Ar:Kr ion laser was focused onto the back side of wafer 60 as shown in FIG. 4A. Laser beam 65, having excitation wavelength of 488 nm, created a nonradiating near field on the other side film 62 near a fluorophore 68. A microscope objective captured the fluorescent far-field radiation of 560 nm, which was recorded in a time-dependent manner by a photomultiplier. This time-dependent signal then gave a record of the passage of the object over the slit with a spatial resolution roughly equal to the width of the slit 36.

FIG. 9 shows a response of the photomultiplier for 0.5 micron balls passing a 2.0 micron wide slit (curve 94A) and 0.1 micron wide slit (curve 94B). Curves 94A and 94B represent the voltage of the photomultiplier as a function of time. As expected, the smaller slit produces the narrower curve 94B, which is the minimum response of this setup.

FIGS. 10A through 10C show the imposition of fluorescent beads and yoyo-1 stained T4 DNA simultaneously passing through two nanoslits which are spaced 10 μm apart FIG. 10A shows two intensity peaks of a bead passing through the first slit and then through the second slit. FIG. 10B shows a partly uncoiled strand of DNA passing through the delivery channel. Broader peaks 99A and 99B are due to the geometry of the DNA coil. The passage of the fluorescent bead is superimposed on the DNA signal. FIG. 10C shows a highly extended DNA in transit through three slits, 36A, 36B and 36C. Again, for reference, the signal from a fluorescent bead is superimposed of the DNA signal. Broader peaks 97A, 97B and 97C are due to the geometry of the DNA coil.

Figure 11A:
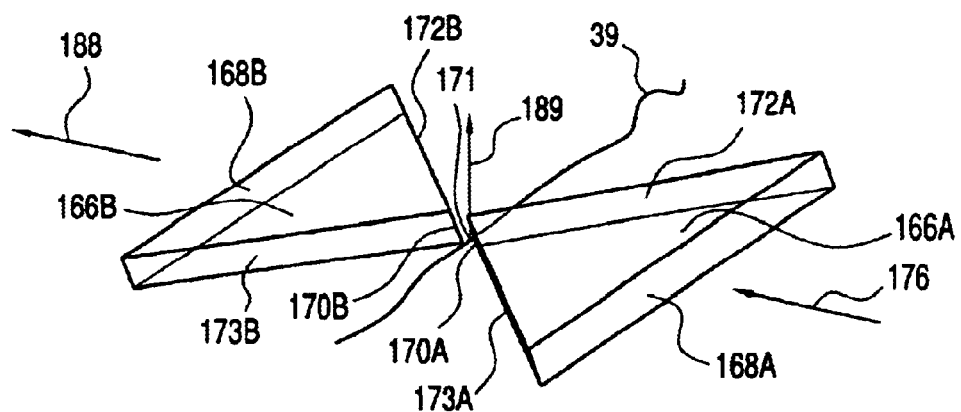
FIG. 11A is a perspective view of the optical waveguides shown in FIG. 11.
Figure 11:
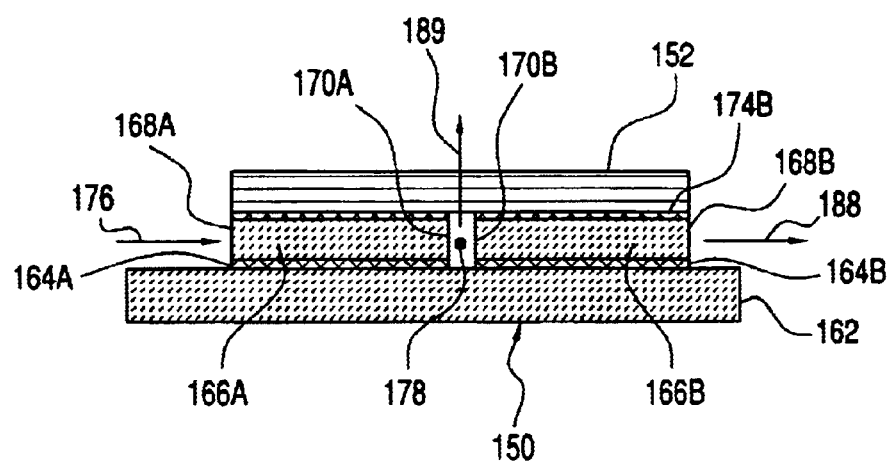
FIG. 11 is a cross-sectional view of the central line of optical waveguides according to another embodiment of the first interaction station.

FIG. 11 is a cross-sectional view of quartz wafer 150 with waveguide 160 taken along a central axis of the waveguide. Waveguide 160 includes and two waveguides 166A and 166B with a rectangular cross-section fabricated on quartz wafer 150. Rectangular waveguides 166A and 166B may be rectangular dielectric waveguides that use two dielectric materials with different refractive indexes and confine light in a core material with a larger refractive index ($n_2$) than the refractive index ($n_1$) of the surrounding dielectric material ($n_2 > n_1$). Alternatively, rectangular waveguides 166A and 166B may be rectangular mirror waveguides that use a dielectric core material surrounded by a metallic material, or waveguides 166A and 166B by be formed by a combination of the two types of waveguides.

The rectangular dielectric waveguides ideally achieve the total internal reflection of light propagation, where the incident angle $\theta_1 > \theta_c$. To confine the introduced light using total internal reflection, interaction station 40 uses a triangular waveguide with a very small angle at the tip. Rectangular mirror waveguides usually exhibit a higher loss depending on the quality of the metallic mirrors. Rectangular mirror waveguides convey light up to a wavelength ($\lambda$) equal twice the height (h) of the waveguide ($\lambda = 2 \cdot h$). Thus these waveguides have a height designed for propagation of light in a selected range of wavelengths useful for polymer examination. For further details see "Fundamentals of Photonics," by Bahaa E. A. Saleh and Malvin Carl Teich, John Wiley & Sons, 1991.

Figure 11B:
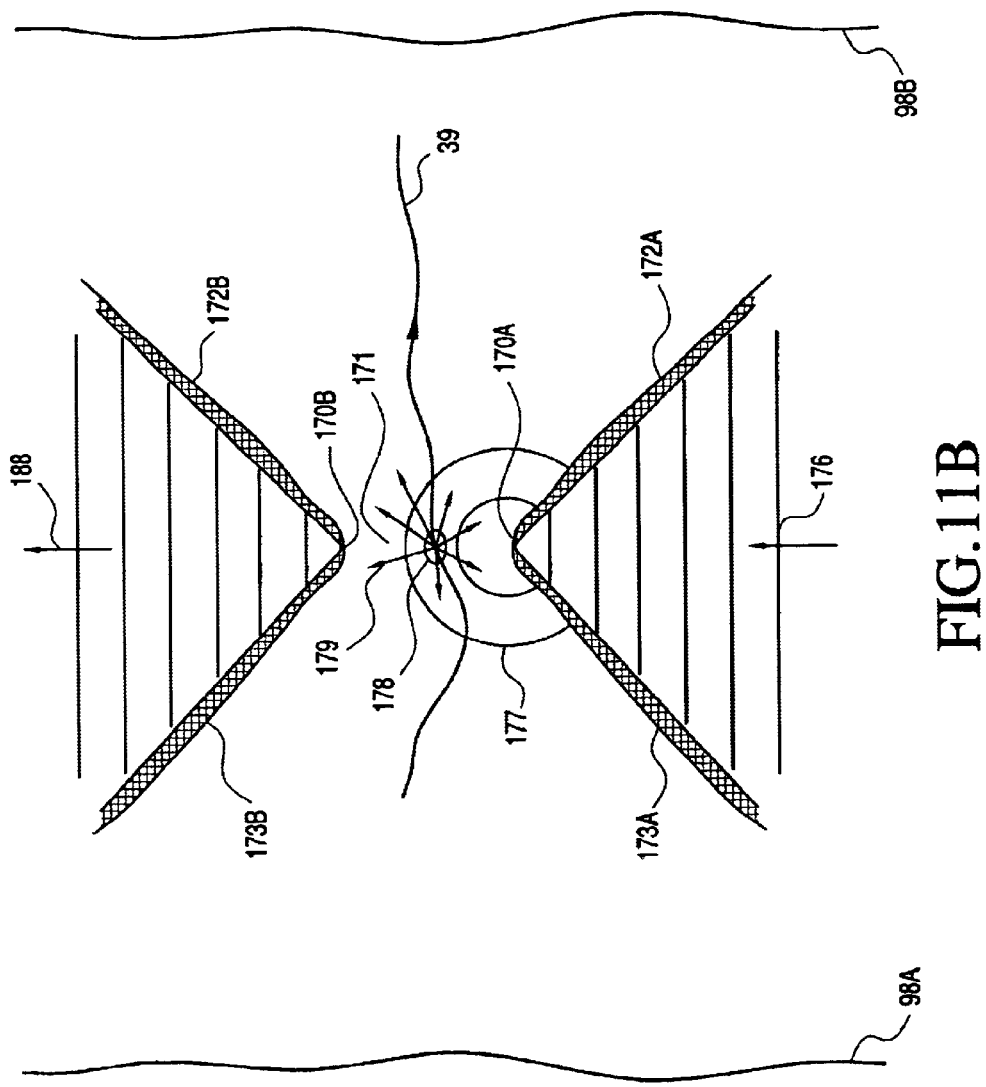
FIGS. 11B and 11C illustrate the interaction of with a linearized polymer with evanescent radiation emitted from the optical waveguide.

As shown in a perspective view in FIG. 11A, waveguides 166A and 166B are located symmetrically with their tips 170A and 170B aligned along the symmetry axis defining a nanochannel 171 (shown in FIG. 11B). Nanochannel 171 has a width in the range of 2 nm to 100 nm, and preferably in the range of 5 nm to 50 mm. Gold wires 98A and 98B (shown in FIG. 11B) are spaced about 3 to 25 millimeters from nanochannel 171. Alternatively, as shown in FIG. 11C, the two waveguide arrangement may be replaced by a single waveguide with an opposite electrode forming a wider channel in the range of 100 nm to 1 $\mu$m.

Figure 12:
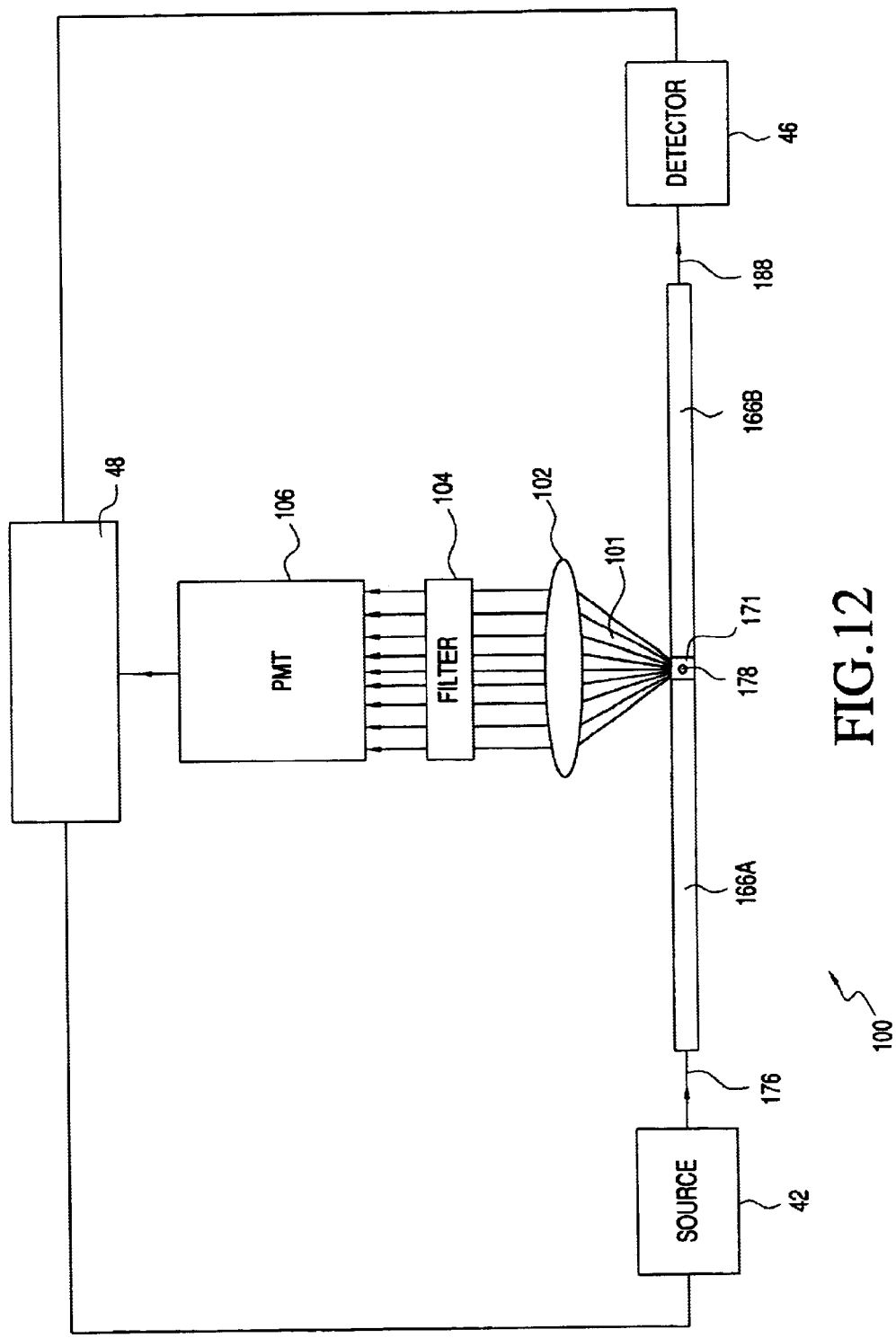
FIG. 12 illustrates optical systems for near-field and far-field detection as used with the optical waveguide of FIG. 11.

Triangular waveguides 166A and 166B shown in FIGS. 11 and 11A are about 10 $\mu$m wide, 5000 $\mu$m long, and over 1 $\mu$m high and are made of $SiO_2$. Waveguides 166A and 166B are isolated from substrate 162 by metallic layers 164A and 164B and from a glass cover 152 by metallic layers 174A and 174B, respectively. (Alternatively, metallic layers 164A and 174A for waveguide 166A, or metallic layers 164B and 174B waveguide 166B, may be replaced by dielectric layers with a lower refractive index.) The introduced plane wave 176 is coupled into triangular waveguide 166A at an input side 168A and undergoes internal reflection at waveguide sides 172A and 173A as it is transmitted toward waveguide tip 170A. Waveguide tip 170A emits waves of evanescent radiation (illustrated in FIG. 11B) into nanochannel 171. In nanochannel 171, the evanescent radiation interacts with individual units of polymer 39 producing radiation with a characteristic signal. For example, the evanescent radiation interacts with a fluorophore located next to a specific unit of polymer 39. Triangular waveguide 166B collects the radiation including the characteristic signal (e.g., fluorescent radiation) from nanochannel 171 and transmits this radiation toward coupling region 168B. As the collected radiation propagates inside waveguide 166B, the radiation nay undergo the total internal reflection at the triangular sides 172B and 173B. The output side 168B, providing radiation 188, is optically coupled to optical detector 46 (FIG. 1). Furthermore, the radiation from nanochannel 171 is also emitted in the direction 189, through glass cover 152. Another, external optical detector, located few millimeters to few centimeters above nanochannel 171 detects far-field radiation 189, as shown in FIG. 12.

FIG. 11B is a cross-sectional view of two triangular waveguides 166A and 166B surrounded by metal layers on each side, wherein the cross-hatched pattern denotes a metal layer on waveguide sides 172A, 172B, 173A, and 173B. However, the metal layer does not cover completely the apex of tips 170A and 170B of triangular waveguides 166A and 166B. The metal layer at tips 170A and 170B my be removed during the etching or milling process that is used to create nanochannel 171, as described below. Waveguide 166A conveys introduced light beam 176 to tip 170A by confining substantially the entire wave inside the $SiO_2$ volume. At tip 170A, waveguide 166A emits evanescent waves 177, which are attenuated as $q^{-1}$ wherein $q = n_{1,2} \omega/c[(\sin\theta_1/\sin\theta_c)^2 - 1]^{1/2}$ in a dielectric waveguide (see, e.g., "Optical Waves in Layered Media" by P. Yeh, John Wiley & Sons, 1988). Thus the evanescent wave is attenuated over a distance of only one or two wavelengths for the total internal reflection ($\theta_1 > \theta_c$). Waves of evanescent radiation 177 interact with the units of polymer 39 passing through nanochannel 171. For example, evanescent waves 177 interact with a fluorophore 178 selectively attached to a selected unit of polymer 39. Fluorophore 178 emits fluorescent radiation 179 propagating in all directions. Fluorescent radiation 179 is collected by waveguide 166B and conveyed to detector 46 (FIG. 1).

Figure 11C:
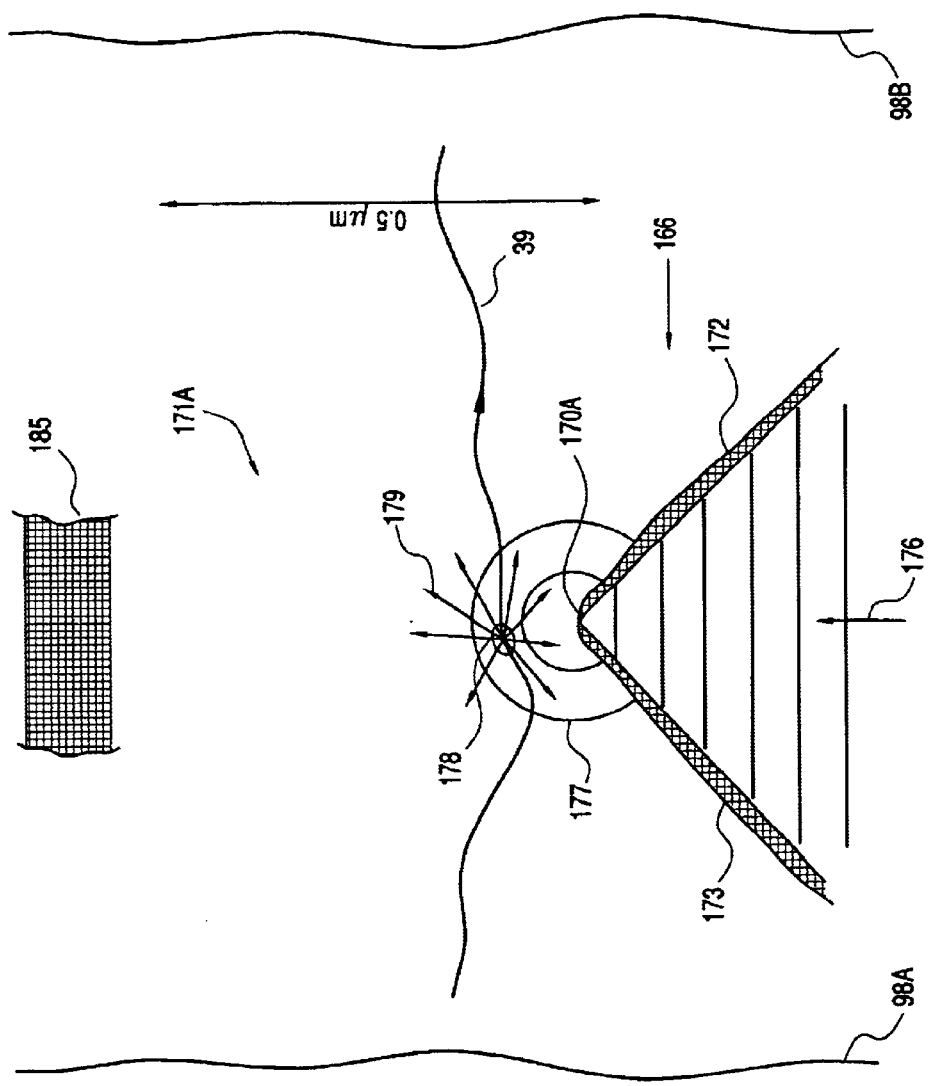

FIG. 11C is a cross-sectional view of another embodiment using a single triangular waveguide 166 and a metal electrode 185. A channel 171A formed between waveguide 166 and metal electrode 185 is about 0.5 $\mu$m, which is significantly larger than nanochannel 171. Triangular waveguide 166 is surrounded by metal layers on all sides and is fabricated similarly as waveguides 166A and 166B (FIG. 11A), wherein the cross-hatched pattern denotes a metal layer on waveguide sides 172 and 173. Similarly as for waveguide 166A, tip 170A emits evanescent waves 177, which are attenuated over a distance of only one or two wavelengths. Therefore, polymer 39 has to be pulled closer to tip 170 than electrode 185 to irradiate fluorophore 178 with evanescent waves 177.

Polymer 39 is pulled closer to tip 170 using dielectric forces created by applying AC field to electrode 185 and waveguide 166, i.e., metal layers 164 and 174, in addition to the DC field applied across wires 98A and 98B. The AC field applied capacitively with respect to the DC field generates inhomogeneous field in nanochannel 171 A as described above in connection with FIG. 4A.

FIG. 12 illustrates an optical system 100 for detecting near field and far field radiation emitted from nanochannel 171. Optical source 44 emits light beam 176, which is focused onto input side 168A of waveguide 166A using techniques described in connection with FIGS. 13 through 13B. After the interaction of evanescent waves 176 with polymer 39, the near field radiation is collected by waveguide 166B and optically coupled to optical detector 46 from output side 168B. The far field 100, emitted in direction 189, is collected by a lens 102, filtered by a tunable filter 104 and provided to a PMT detector 106. Optical source 42, such as an LED or a laser diode may be incorporated onto quartz wafer 150. This arrangement would eliminate the need for an external optical source which is to be aligned with input side 168A. The optical sources are made using a direct bandgap material, for example GaN for generating UV radiation, or GaP:N for generating radiation of a green wavelength.

Quartz wafer 150 may also include an integrated optical detector 46 in order to avoid external setup for detection and filtering. An integrated avalanche photodiode or a PIN photodiode, together with an insitu filter for filtering out the excitation wavelength, receive light beam 188. Various integrated optical elements are described in "Integrated Optoelectronics—Waveguide Optics, Photonics, Semiconductors," by Karl Joachim Ebeling, Springer-Verlag, 1992. For example, a corrugated waveguide is used as a contradirectional coupler so that light within a narrow frequency band will be reflected back resulting in a filtering action. Another filter is made using two waveguides with different dispersion relations in close proximity. Light from one waveguide will be coupled into the other for wavelengths for which there is a match in the index of refraction. By applying a voltage to the waveguides, the dispersion curve is shifted and the spectrum of the resulting filter is altered providing a tunable filter.

In another embodiment, the optical system 110 is an ultra fast, highly sensitive spectrophotometer capable of detecting fluorescence from a single fluorophore as described above.

In another embodiment, the optical system 120 uses radiation modulated at frequencies in the range of 10 MHz to 1 GHz as described above.

Figure 13:
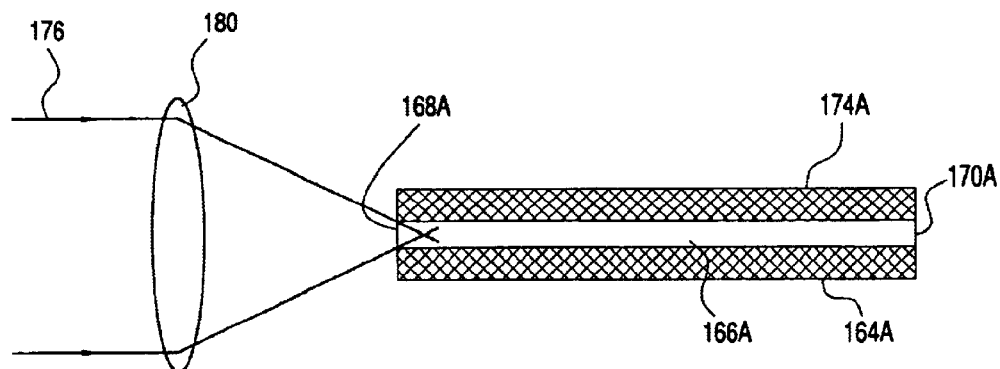
FIGS. 13, 13A and 13B illustrate coupling of electromagnetic radiation into the optical waveguide of FIG. 11.
Figure 13A:
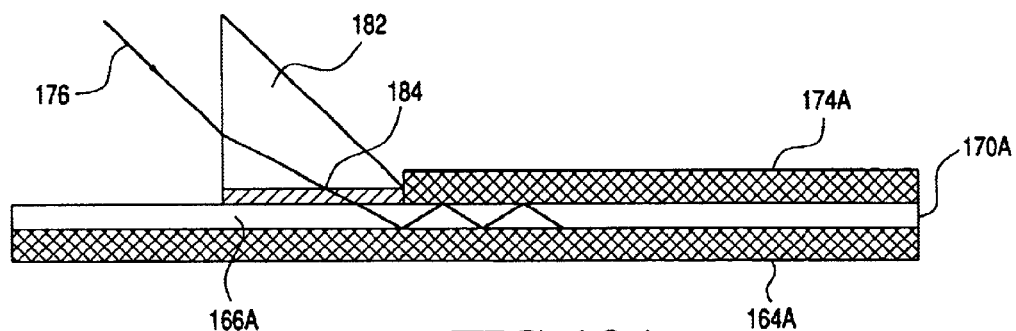
Figure 13B:
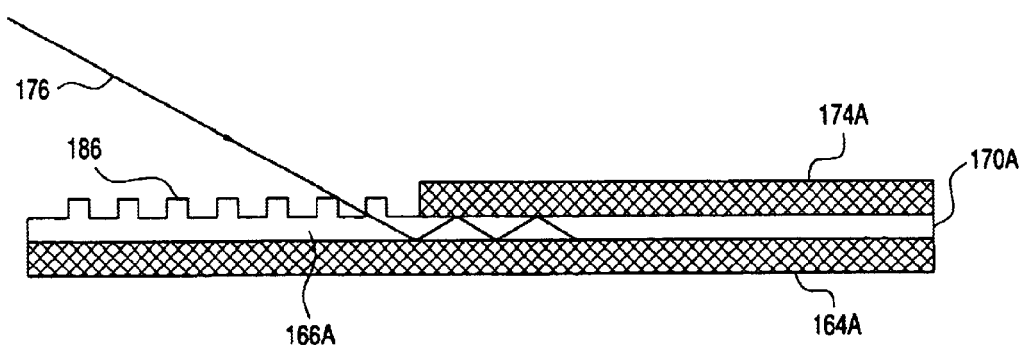

FIGS. 13 through 13B show different types of coupling of light from an external optical source into a waveguide. Referring to FIG. 13, lights source 42 emits light beam 176, which is focused onto the input side 168A of triangular waveguide 166A using a focusing lens 180. Alternatively, referring to FIG. 13A, a prism 182 is used to couple light beam 176 into triangular waveguide 166A. Light beam 176 is diffracted by prism 182 and undergoes inside the total internal reflection. Prism 182 is located on the surface of $SiO_2$ volume 166A and is arranged to optically couple beam 176 across a layer 184 into waveguide 166A. Referring to FIG. 13B, alternatively, a diffraction grating 186 is used to couple light beam 176 into triangular waveguide 166A. Grating 186 is fabricated on waveguide 166A so that it diffracts light beam 176 toward tip 170A. Alternatively, an optical fiber couples light beam 176 to triangular waveguide 166A. Different ways to couple light into a waveguide are described in Fundamentals of Optics, by Clifford R. Pollock, Richard D. Irwin Inc., 1995.

Waveguides 166A and 166B are fabricated on quartz or another insulating material to avoid electrical currents in substrate 150. To achieve the required high definition in the nanochannel region (i.e., 10 nm resolution), the fabrication process uses UV lithography alone or in combination with deep UV lithography, e-beam lithography or X-ray lithography. The contiguous waveguide is first defined using standard UV lithography, and then nanochannel (or microchannel 171A described in connection with FIG. 11C) is defined in separate e-beam or X-ray lithography steps. In waveguide embodiments that include a radiation slit at tips 170A and 170B, the slit (or a hole) is fabricated by creating a concave shape of the photoresist (i.e., an undercut) at the very tips 170A and 170B of waveguides 166A and 166B, and by creating a convex shape of the photoresist at the sides 172A, 173A, 172B and 173B before evaporating the metal. Thus, the convex sides will be covered by the evaporated metal, but not the concave tip. Alternatively, the small tip (the small hole) is fabricated by first creating a very thin wall and then using lift-off or etching to create a metal film with the small slit over the wall. When using e-beam lithography, metal hard masks are used to keep the resist thickness down and the resolution high, as is known in the art.

Figure 14A:
Figure 14B:
Figure 14C:
Figure 14D:
Figure 14E:
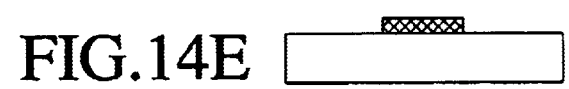
Figure 14F:
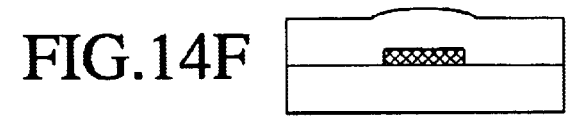

Referring to FIGS. 14A through 14K that are side views along the central line of waveguides 166A and 166B are fabricated as follows: To improve adhesion of the resist to the wafers, the wafers are primed in hexamethyldisiloxane (HMDS) for 34 minutes (FIG. 14A). Then, a photoresist Shipley 1830 is spun onto the wafers at 4000 rpm 60 sec to achieve a 1.3 micron thick resist and the wafers are baked on a hotplate at 115 C. for 60 sec to harden the resist (FIG. 14B). The photoresist is exposed in a high resolution mask aligner such as a 5×g-line stepper and baked in a pressurized $NH_3$ oven. This reverses the positive tone of the photoresist and provides the necessary backward leaning profile (i.e., the undercut shown in FIG. 14C) for the subsequent lift-off process. The wafer is flood exposed for 1 min in the HTG/contact aligner with 405 nm light and developed with Microposit 321 for 1 min. Referring to FIG. 14D, a 1000 Angstrom Al layer is deposited and the lift-off is performed using Microposit 1165 resist remover or acetone at room temperature (FIG. 14E). All resist residues are removed using the resist descum process in the Branson Barrel etcher, 0.6 Torr $O_2$ at 150 W RF power.

Figure 14G:
Figure 14H:
Figure 14I:
Figure 14J:
Figure 14K:
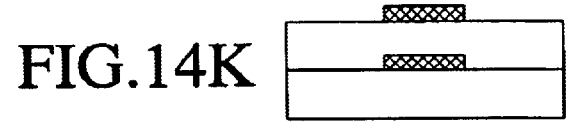

Referring to FIGS. 14F through 14K, the $SiO_2$ waveguide is created as follows: A 1 micron $SiO_2$ is deposited using plasma enhanced chemical vapor deposition (PECVD) at T=240 C., 450 mTorr, 50 W RF power using 15 sccm silane, 50 sccm $N_2O$. The $SiO_2$ layer is planarized by chemical mechanical polishing (CMP), as shown in FIG. 14G. The top metal mask is defined by spinig photoresist Shipley 1830 onto the wafers at 4000 rpm for 60 sec to achieve a 1.3 micron thick resist and baking it on a hotplate at 115° C. for 60 sec. The resist is exposed in a high resolution mask aligner, such as a 5×g-line stepper, and baked in a pressurized $NH_3$ oven. This reverses the positive tone of the photoresist and provides the necessary backward leaning profile (i.e., the undercut) for the subsequent lift-off process, as shown in FIG. 14I. The resist is flood exposed for 1 min in the HTG/contact aligner by 405 nm light and developed in Microposit 321 for 1 min. As shown in FIG. 14J, a layer of 1000 A Al metal is deposited. The excess metal is removed by a lift-off using the Microposit 1165 resist remover or acetone at room temperature.

FIGS. 15A through 15G are side views along the central line and FIGS. 16A through 16G are side views along a line perpendicular to the central line. The PMMA resist 496K is spun onto the wafers at 2500 rpm to achieve a 200 nm thick resist and bakes on a hotplate at 180° C. for 60 min. to harden the resist. The PMMA is exposed by the e-beam system to create the pattern in the nanochannel region. The exposed PMMA resist is developed in IPA:MIBK 3:1 for 1 min and a 1000 A layer of Al metal is deposited as shown in FIG. 15C. After performing the lift-off of the excess metal in acetone, the waveguide is etched, but without the microchannel pattern, in the Plasma Therm 72 etcher using reactive ion etching (RIE) in $CHF_3$ (50 sccm)+$O_2$ (2 sccm) at 200 W RF power and 40 mTorr, >1 micron to create a wall shown in FIG. 15B. The bottom metal is wet etched in the solution of 16:$H_2PO_4$; 1:$HNO_3$; 1:acetic acid; 2:water; wetting agent, or dry etched in Cl. The remaining resist is removed in a Branson Barrel $O_2$ plasma etcher at 1000 W RF power for 15 min. The aluminum is removed in a wet etch using 16:$H_2PO_4$; 1:$HNO_3$; 1:acetic acid; 2:water; wetting agent.

The deposition of the top Al layer over the waveguide is shown in FIGS. 15E through 15G and 16D through 16G. Referring to FIGS. 15E and 16D, a photoresist Shipley 1830 is spun onto the wafers at 4000 rpm for 60 sec to achieve a 1.3 micron thick resist and baked on a hotplate at 115° C. for 60 sec. to harden the resist. The resist is exposed in a high resolution mask aligner, such as a 5×g-line stepper, and baked in a pressurized $NH_3$ oven. This reverses the positive tone of the photoresist and provides the necessary backward leaning profile (i.e., the undercut) for the subsequent lift-off process. The resist is flood exposed for 1 min in the HTG/contact aligner 405 nm light and developed in Microposit 321 for 1 min. A 1000 A Al layer is deposited as shown in FIGS. 15F and 16F. The excess metal is lifted-off using the Microposit 1165 resist remover or acetone at room temperature.

A layer of Cr metal is deposited on the top of the device as follows. First, a mask for the nanochannel was etched and then the Shipley 1830 resist was spun onto the wafers at 4000 rpm for 60 sec to achieve a 1.3 micron thick resist and baked on a hotplate at 115° C. for 60 sec to harden the resist. The resist was exposed in a high resolution mask aligner, such as a 5×g-line stepper, and baked in a pressurized $NH_3$ oven. This process reverses the positive tone of the photoresist and provides the necessary backward leaning profile (i.e., the undercut) for the subsequent lift-off process. The resist was flood exposed for 1 min in the HTG/contact aligner using 405 nm light and developed in Microposit 321 for 1 min. Then, a 1000 Å Cr layer was deposited and a lift-off of excess metal was performed in the Microposit 1165 resist remover or acetone at room temperature. A PMMA 496K resist was spun onto the wafers at 2500 rpm to achieve a 200 nm thick resist and baked on a hotplate at 180° C. for 60 min. to harden the resist. The resist was exposed in the e-beam system to define the desired pattern, and the wafer was developed in IPA:MIBK 3:1 for 1 min. Then, a 1000 Å Cr layer was deposited and the lift-off of excess metal was performed in the Microposit 1165 resist remover or acetone at room temperature.

Nanochannel 171 was crated by etching the first metal layer (i.e., the Al layer) in a Cl based dry etch, wherein Cr acts as an etch mask. Then, the $SiO_2$ was etched in Plasma Therm 72 using reactive ion etching (RIE) in CHF3 (50 sccm)+$O_2$ (2 sccm) at 200 W RF power and 40 mTorr, >1 micron to create a wall. The bottom metal layer was etched in a Cl based dry etch and the remaining Cr was removed using a wet etch. Alternatively, nanochannel 171 can be fabricated by focussed ion beam milling to define the gap and the aperture in the tip.

For DNA sequencing, the individual molecules can be selectively labeled as described in the PCT application PCT/US98/03024 filed on Feb. 11, 1998, which is incorporated by reference. The sequencing is done using a combination of single-stranded DNA molecules (ssDNA), which have been hybridized with fluorescently tagged oligonucleotides of test sequences. When hybridization occurs, the tagged sequence is now at a fixed position on the DNA molecule. The process can use three tags: "start" and "stop" tags, which signal the 3' and 5' beginning and end of the ssDNA, and the tagged oligo which is used for sequencing. By observing a large population of these tagged molecules using a spectrum of oligonucleotide sequences as they pass through the microchannel and recording the position of the oligonucleotide labels, the system obtains the sequence of the molecule at an unprecedented level of speed, accuracy and low molecule concentration.

Figure 17:
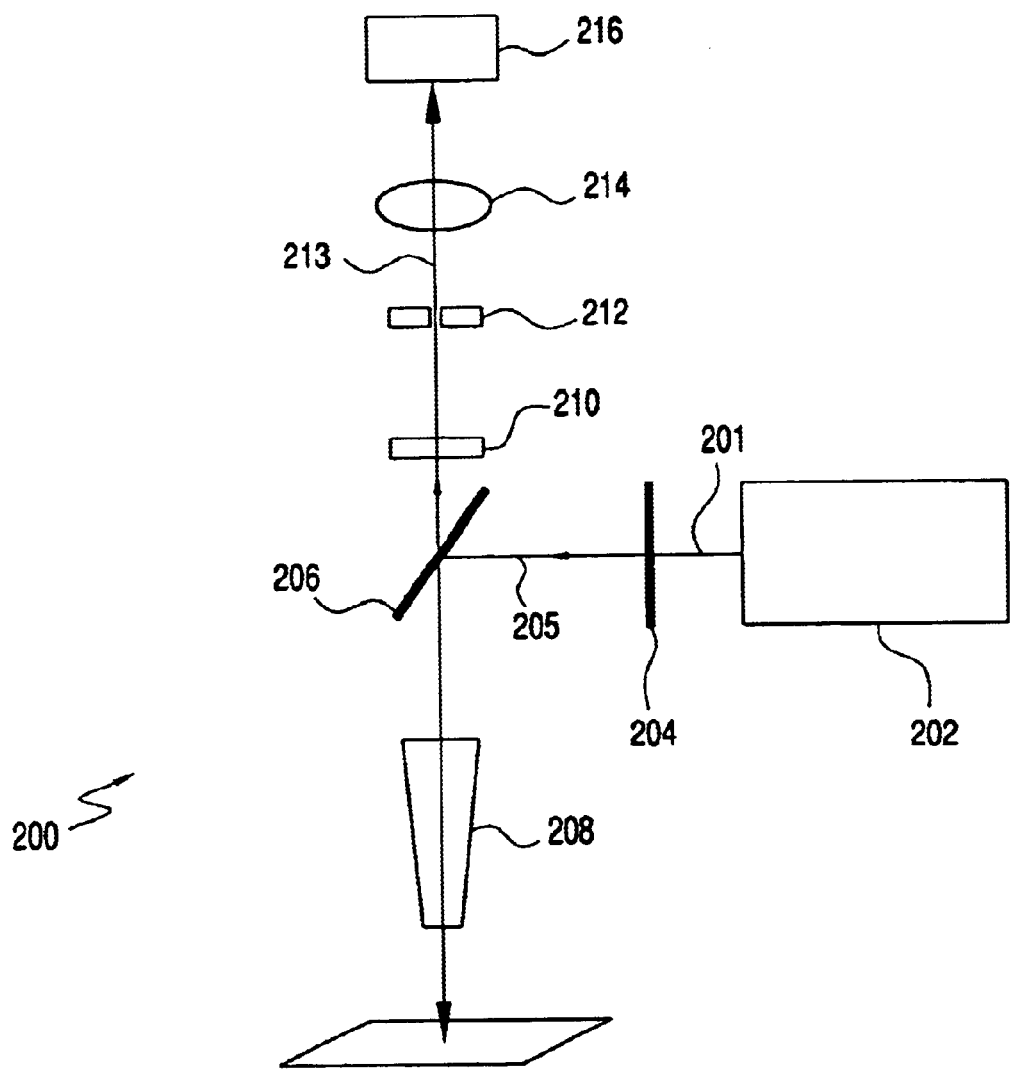
FIG. 17 is a schematic of an optical apparatus which utilizes confocal fluorescence illumination and detection for linear analysis of polymers.

Another embodiment of the present invention is shown in FIG. 17. An optical apparatus 200 utilizes confocal fluorescence illumination and detection. Confocal illumination allows a small optical volume (on the order of picoliters) to be illuminated. Both Raleigh and Raman scattering are minimized using a small probe volume. Optical apparatus 200 includes a light source 202, a filter 204, a dichroic mirror 206, an objective 208, a narrow band pass filter 210, a pinhole 212, a lens 214, and a detector 216. Light source 202, which is a 1 mW argon ion laser, emits a laser beam 201, which passes through filter 204. Filter 204 is a laser line filter that provides a focused beam of a wavelength of about 514 nm. The filtered beam 205 is reflected by dichroic mirror 206 and is focussed by objective 208 onto a region of a DNA sample or another polymer. Objective 208 is a 100×1.2 NA oil immersion objective.

The DNA sample is a straightened DNA molecule with one or several units tagged by a fluorescent tag. The fluorescent tag on the DNA can be one of several dyes including Cy-3, tetramethylrhodamine, rhodamine 6G, and Alexa 546. In addition, intercalator dyes can be used such as TOTO-3 (Molecular Probes).

The excited tag provides a fluorescence emission that is passed through dichroic mirror 206, narrow bandpass filter 210 (e.g., manufactured by Omega Optical) and is focused onto a 100 $\mu$m pinhole 212. The fluorescent light 213 is focussed by aspheric lens 214 onto detector 216, which is an avalanche photodiode (e.g., manufactured by EG&G Canada) operating in the photon counting mode. The output signal from the photodiode is collected by a multichannel scalar (EG&G) and analyzed using a general purpose computer.

Figure 18:
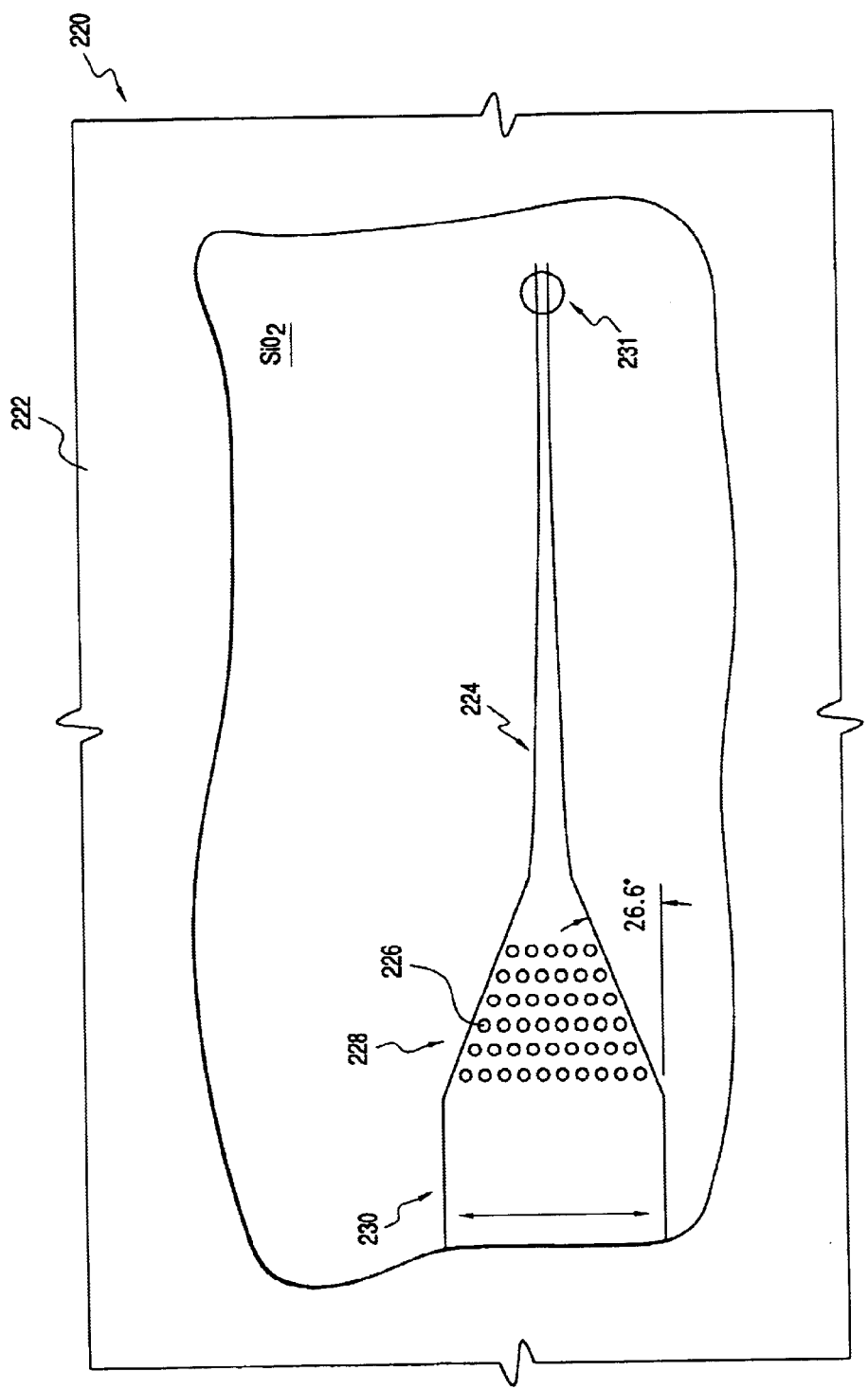
FIG. 18 is a top view of another embodiment of the alignment station for aligning and stretching polymer.

The confocal apparatus is appropriate for quantitative applications involving time-off-flight. Such applications include measuring distances on the DNA, detecting tagged sequences, and determining degrees of stretching in the DNA. Single fluorescent molecules can be detected using the apparatus. Alternatively, an imaging apparatus uses an intensified CCD (ICCD, Princeton Instruments) mounted on a microscope. FIG. 18 shows a presently preferred embodiment of alignment station 220 for aligning and stretching polymers before they reach an interaction station 231, where they interact with optical radiation. Alignment station 220 is fabricated on a quartz wafer, which may be covered with a metal layer 222 (e.g., aluminum, gold, silver) Alignment station 220 includes a triangular microchannel 224, microspot region 228, and an entrance region 230, all fabricated on the surface.

Entrance region 230 is about 50 micron wide and is in communication with micropost region 228. Micropost region 228 includes several alignment posts 226. Alignment posts 226 have a circular cross-section and are about 1 micron in diameter. Alignment microposts 226 are spaced about 1.5 microns apart in 12 to 15 rows. Micropost region 228 is canted at about 26.6 degrees.

Microposts 226 are located about 100 $\mu$m to 5,000 $\mu$m (and preferably about 1,000 $\mu$m to 3,000 $\mu$m) from the interaction station, where the units of the polymer (e.g. DNA) interact with optical radiation. Microchannel 224 is a region of constant x-direction shear that maintains the polymer in extended conformation after release from microposts 226. The electric field pulls the examined polymer through microchannel 224.

A very effective technique of stretching a polymer (e.g., DNA) uniformly is to have an obstacle field inside the tapered microchannel 224, followed by a constant-shear section to maintain the stretching obtained and straighten out any remaining coiling in the polymer. The preferred embodiment is a structure that combines microposts with two regions of different funnel designs as shown in FIG. 18. Pressure flow is the preferred driving force because of the predictable behavior of fluid bulk flow.

A constant shear rate, or change in average velocity with distance in the channel, is defined as S:

$$u/x=S$$

where x is the distance down a substantially rectangular channel, and u is the average fluid velocity, which is computed from the overall fluid flow (Q) and the cross-sectional area (A) of the channel as follows:

$$u=Q/A$$

In one embodiment where the channel cross-section is rectangular, the channel may be defined by a constant height, H and width, W such that the cross-sectional area A=HW, and the average fluid velocity is given by:

$$u=Q/HW$$

Applying the boundary condition that the fluid flow must be continuous, Q is constant Hence, u is inversely proportional to W. This relationship can be substituted into the original expression for S to determine a relationship between the shear rate and the width:

$$S=u/x=Q/H/x(1/W)=(-Q/HW^2)(dW/dx)$$

$$dW/dx=(-SH/Q)(W^2)$$

Integrating this expression, it is found that:

$$W=(SHx/Q+C)-1$$

where C is a constant of integration determined by the original width of the channel (boundary condition). This equation for the width of the channel is used to define a channel beyond a post structure.

Other embodiments are within the following claims:

What is claimed is:

1. A system for optically analyzing a polymer of linked units comprising:
   (a) an optical source constructed to emit optical radiation of a known wavelength;
   (b) a fluid-filled microchannel adapted to transport individual molecules of said polymer being analyzed;
   (c) an alignment station constructed and arranged to at least partially straighten the individual polymer molecules, said alignment station being in fluid communication with the microchannel and including means for accelerating the fluid passing therethrough;
   (d) an interaction station constructed to receive said optical radiation and produce a localized radiation spot from said optical radiation, said interaction station being also constructed to sequentially receive said at least partially straightened polymer molecules and arranged to irradiate sequentially said molecules at said localized radiation spot, whereby, when irradiated, the polymer molecules emit detectable characteristic signals;
   (e) an optical detector for receiving said characteristic signals resulting from interaction of said molecules at said localized radiation spot; and
   (f) a processor in communication with the optical detector constructed and arranged to analyze said polymer based on said received characteristic signals.

2. The system of claim 1, wherein said interaction station includes at least one slit having a submicron width arranged to produce said localized radiation spot in the microchannel at a region through which the molecules of polymer are transported.

3. The system of claim 1, wherein said width is in the range of 10 nm to 100 nm.

4. The system of claim 2, further including a polarizer and wherein said optical source includes a laser constructed to emit a beam of said radiation, said polarizer being arranged to polarize said beam prior to reaching said slit.

5. The system of claim 4, wherein said polarizer is arranged to polarize said beam in parallel to said width of said slit.

6. The system of claim 4, wherein said polarizer is arranged to polarize said beam perpendicular to said width of said slit.

7. The system of claim 2, wherein said interaction station includes a plurality of slits intersecting said microchannel.

8. The system of claim 2, further including a set of electrodes constructed and arranged to provide electric field for advancing said units of said polymer through said microchannel.

9. The system of claim 8, wherein said electrodes are internal electrodes.

10. The system of claim 8, wherein said electrodes are external electrodes.

11. The system of claim 2, wherein said slit is several micrometers long.

12. The system of claim 2, wherein said alignment station constructed and arranged to straighten said polymer molecules and provide said straightened polymer molecules to said microchannel, said alignment station including several microposts of about 1 µm in diameter and being spaced about 0.5 µm to 5 µm apart.

13. The system of claim 2, further including an alignment station constructed and arranged to straighten said polymer molecules and provide said straightened polymer molecules to said microchannel, said alignment station including several microposts being located at a distance of about 5 µm to 500 µm from said slit.

14. The system of claim 13, wherein said microposts are spaced 0.5 µm to 2.5 µm apart.

15. The system of claim 1, wherein said interaction station is constructed to sequentially receive said molecules being selectively labeled with a radiation sensitive label producing said characteristic signals at said localized radiation spot.

16. The system of claim 15 wherein said radiation sensitive label includes a fluorophore.

17. The system of claim 1 wherein said interaction station includes a slit having a width in the range of 1 nm to 500 nm, said slit producing said localized radiation spot.

18. The system of claim 1 wherein said optical source is a laser and said system further including an acousto-optic tunable filter arranged to select said wavelength.

19. The system of claim 18 wherein said wavelength is an excitation wavelength of a fluorophore selectively coupled to said units and said characterstic signal being a fluorescent wavelength emitted by said fluorophore.

20. The system of claim 19 further including a notch filter arranged to transmit only said fluorescent wavelength to said optical detector.

21. The system of claim 1 wherein said optical source is constructed to emit said wavelength in the range of ultraviolet to infrared wavelengths.

22. The system of claim 1 wherein said optical detector includes one of the following a photodiode, an avalanche photodiode, a photomultiplier, a PIN diode, and a CCD.

23. The system of claim 1 wherein said processor is arranged to evaluate said characteristic signal being a flourescent lifetime.

24. The system of claim 1 wherein said processor is arranged to evaluate said characteristic signal being a flouescent wavelength.

25. The system of claim 1 wherein said processor is arranged to evaluate said characteristic signal being intensity of said detected optical radiation.

26. The system of claim 1 wherein said processor is arranged to evaluate said characteristic signal being a time dependent property of said detected optical radiation.

27. A method for optically analyzing a polymer of linked units comprising the steps of:
   (a) sequentially passing individual molecules of said polymer through a fluid-filled microchannel, the microchannel being in fluid communication with an alignment station;
   (b) at least partially straightening said molecules as they pass through the alignment station;
   (c) accelerating the fluid passing through the alignment station;
   (d) generating optical radiation of a known wavelength to produce a localized radiation spot;
   (e) irradiating sequentially said molecules of said at least partially straightened polymer at said localized radiation spot whereby, when irradiated, the polymer molecules emit detectable characteristic signals;
   (f) detecting such characteristic signals; and (g) analyzing said polymer based on said detected characteristic signals.

28. The method of claim 27, wherein said producing said localized radiation spot includes optically coupling said generated light to a nanoslit having a width in the range of about 1 nm to 500 nm.

29. The method of claim 27, wherein said step of producing said localized radiation spot includes optically coupling said generated light to several nanoslits each having a length oriented perpendicularly to said microchannel.

30. The method of claim 24, wherein said step of producing said localized radiation spot includes generating said light in form of a laser beam and polarizing said laser beam to be oriented in parallel to said width of said slit.

31. The method of claim 28, wherein said step of producing said localized radiation spot includes generating said light in form of a laser beam and polarizing said laser beam to be oriented in perpendicular to said width of said slit.

32. The method of claim 27, wherein said step of partially straightening said polymer molecules includes passing the molecules of polymer through a plurality of microposts of said alignment station, said plurality of microposts being spaced 0.5 to 5 microns apart and being located 5 to 100 micron from said localized radiation spot.

33. The method of claim 27 wherein said passing said polymer through said microchannel includes employing electric field.

34. The method of claim 27 wherein said producing said localized radiation spot includes optically coupling said generated light to a nanoslit having a width less than one $\mu$m.

35. The method of claim 27 further comprising the step of labeling selected polymer molecules with a radiation sensitive label, and wherein said step of detecting said characteristic signals includes collecting said radiation of said label including said characteristic signals over time while said molecules are passing through said microchannel.

36. The method of claim 35, wherein said label includes a fluorophore and wherein said step of detecting said characteristic signals includes filtering said signals to provide to an optical detector only radiation excited by said fluorophore.

37. The method of claim 27 wherein said generating includes generating said optical radiation of said wavelength in the range of ultraviolet to infrared wavelengths.

38. The method of claim 27 wherein said detecting includes using a photodiode detector, an avalanche photodiode detector, a photomultiplier detector, a PIN diode detector or a CCD detector.

39. The method of claim 27 wherein said polymer is a nucleic acid.

40. An article of manufacture used for optically analyzing a polymer of linked units, comprising:

a fluid-filled microchannel adapted to transport said polymer being analyzed;

an alignment station constructed and arranged to at least partially straighten individual molecules of the polymer, said alignment station being in fluid communication with said microchannel and including means for accelerating the fluid passing therethrough; and an interaction station arranged to receive optical radiation emitted from an optical source and produce therefrom a localized radiation spot, said interaction station being further constructed to sequentially receive the individual molecules of said polymer and arranged to irradiate sequentially said molecules at said localized radiation spot to cause the polymer to emit characteristic signals.

41. The article of claim 40, wherein said interaction station includes a microchannel constructed to provide said polymer in a substantially straightened state to said nanoslit.

42. The article of claim 41, wherein said nanoslit has a width less than a wavelength of said radiation.

43. The article of claim 41, wherein said nanoslit has a width in the range of 1 nm to 500 nm.

44. The article of claim 41, wherein said nanoslit has a width in the range of 50 nm to 100 nm.

45. The article of claim 40, wherein the alignment station comprises a plurality of microposts, said microposts being spaced 0.5 $\mu$m to 5 $\mu$m apart and being located 5 $\mu$m to 100 $\mu$m from said localized radiation spot.

46. The article of claim 45, wherein said microposts are located 10 $\mu$m to 200 $\mu$m from said localized radiation spot.

47. The article of claim 46, wherein said microposts are spaced 0.5 $\mu$m to 5 $\mu$m apart.

48. The article of claim 47, wherein said microposts are spaced 1.5 $\mu$m to 2.5 $\mu$m apart.

49. The article of claim 40 wherein said interaction station includes a nanoslit constructed to produce said localized radiation spot.

50. The article of claim 40 further including a set of electrodes constructed and arranged to provide electric field for advancing said units of said polymer through said localized radiation spot.

51. The article of claim 40 wherein said microchannel is less than 1 $\mu$m wide.

\* \* \* \* \*